United States Patent
Croteau et al.

(10) Patent No.: US 6,190,895 B1
(45) Date of Patent: Feb. 20, 2001

(54) NUCLEIC AND AMINO ACID SEQUENCES RELATING TO A NOVEL TRANSKETOLASE, AND METHODS FOR THE EXPRESSION THEREOF

(75) Inventors: Rodney Bruce Croteau, Pullman; Mark Raymond Wildung, Colfax; Bernd Markus Lange; David G. McCaskill, both of Pullman, all of WA (US)

(73) Assignee: Washington State University Research Foundation, Pullman, WA (US)

( * ) Notice: Under 35 U.S.C. 154(b), the term of this patent shall be extended for 0 days.

(21) Appl. No.: 09/146,221

(22) Filed: Sep. 1, 1998

Related U.S. Application Data

(60) Provisional application No. 60/056,033, filed on Sep. 2, 1997.

(51) Int. Cl.[7] .............................. C12N 9/08; C12N 15/00; C07H 21/04
(52) U.S. Cl. .................. 435/193; 435/320.1; 435/252.3; 435/419; 536/23.2
(58) Field of Search .............................. 435/320.1, 252.3, 435/419, 193; 536/23.2

(56) References Cited

PUBLICATIONS

Suggs et al, PNAS, 1981, vol. 78, pp. 6613–6617.*
Database SwissProt, Accession Q38854, submitted by Mandal et al., publicly available Dec. 15, 1998.*
Becker, Nucleic Acids Research, 1990, vol. 18, p. 203.*
Rohmer, M. et al., *Biochem J.*, 295:517–524 (1993).
Zeidler, J.G. et al., *Z. Naturforsch*, 52c:15–23 (1997).
Lois, L.M. et al., Third Terpnet Meeting of the European Network on Plant Isoprenoids, Poitiers, France, May 29–30 (1997).
Mandel, M.A. et al., *Plant J.* 9:649–658 (1996).
Youvan, D.C. et al. *Cell* 37:949–957 (1984).
Kaneko, T. et al., *DNA Res.* 3:109–136 (1996).
Hawkins, C.F. et al., *FEBS Lett.* 255:77–82 (1989).
Kotani, H. et al., *Annu. Rev. Plant Physiol. Plant Mol. Biol.* 49:151–71 (1998).

* cited by examiner

Primary Examiner—Ponnathapu Achutamurthy
Assistant Examiner—Bradley S. Mayhew
(74) Attorney, Agent, or Firm—Christensen O'Connor; Johnson Kindness PLLC

(57) ABSTRACT cDNAs encoding 1-deoxyxylulose-5-phosphate synthase from peppermint (*Mentha piperita*) have been isolated and sequenced, and the corresponding amino acid sequences have been determined. Accordingly, isolated DNA sequences (SEQ ID NO:3, SEQ ID NO:5, SEQ ID NO:7) are provided which code for the expression of 1-deoxyxylulose-5-phosphate synthase from plants. In another aspect the present invention provides for isolated, recombinant DXPS proteins, such as the proteins having the sequences set forth in SEQ ID NO:4, SEQ ID NO:6 and SEQ ID NO:8. In other aspects, replicable recombinant cloning vehicles are provided which code for plant 1-deoxyxylulose-5-phosphate synthases, or for a base sequence sufficiently complementary to at least a portion of 1-deoxyxylulose-5-phosphate synthase DNA or RNA to enable hybridization therewith. In yet other aspects, modified host cells are provided that have been transformed, transfected, infected and/or injected with a recombinant cloning vehicle and/or DNA sequence encoding a plant 1-deoxyxylulose-5-phosphate synthase. Thus, systems and methods are provided for the recombinant expression of the aforementioned recombinant 1-deoxyxylulose-5-phosphate synthase that may be used to facilitate its production, isolation and purification in significant amounts. Recombinant 1-deoxyxylulose-5-phosphate synthase may be used to obtain expression or enhanced expression of 1-deoxyxylulose-5-phosphate synthase in plants in order to enhance the production of 1-deoxyxylulose-5-phosphate, or its derivatives such as isopentenyl diphosphate (BP), or may be otherwise employed for the regulation or expression of 1-deoxyxylulose-5-phosphate synthase, or the production of its products.

23 Claims, 4 Drawing Sheets

SEQUENCE LISTING

<160> NUMBER OF SEQ ID NOS: 12

<210> SEQ ID NO 1
<211> LENGTH: 1949
<212> TYPE: DNA
<213> ORGANISM: Mentha piperita

<400> SEQUENCE: 1

```
aagagcgaga atgcacacaa ttaggcagac atttggatta gcaggtttcc ctaagagaga      60
tgaaagtgct cacgatgcct tcggcgccgg ccatagttct accagtattt ctgctggttt     120
agggatggcg gtggcgagag atttactgca gaagaacaac cacgtcatat cggtgatcgg     180
cgacggcgcc atgacagctg acaagcgta cgaggcctta acaacgccg gattcctcga      240 ttcgaatctc ataatcgttt taaacgacaa caagcaggtg tctctaccca cggccaccgt     300
cgacggccct gcgccgccgg tcggagctct gagcaaagcc ctgaccaagc tgcaagccag     360
cagaaaattc cggcagctcc gcgaagcagc aaagagtatg actaagcaga tgggagcacc     420
ggcacatgaa atagcttcga agttgacaca atacgtgaaa gggatgatgg ggaaaccagg     480
cgcttcactt ttcgaagaac tggggatttta ttacatcgga ccagtcgacg gccataacgt     540
tgaagatctt gtttatattt tcaagaaagt taaggaaatg cctgcgcctg ggcctgttct     600
tattcatatc atcaccgaaa aaggcaaagg ctacccccct gcagaaattg ctgccgacaa     660
aatgcatggg gtggtgaagt ttgatgcgaa aactgggaaa cagatgaaga cgaagaacaa     720
gacgaagtca tacacccagt acttcgccga gtctctggtg gcggaggcgg agcacgacga     780
caagatcgtg gcgatccacg ccgccatggg gggcggcacc gggctcaaca tcttccagaa     840
gcagttcccg gaccggtgct tcgacgtcgg gatcgcggag cagcacgcgg tgacgttcgc     900
cgccggtatg gcggcggagg ggctgaagcc tttctgcgcc atctactcct ccttcctcca     960
gaggggctac gaccaggtgg tccacgacgt cgacctccag aagctcccgg tccggttcat    1020
gatggatcgg gcaggagtcg tcggcgccga cggcgcccacc cactgcggcg ccttcgacac    1080
cacctacatg gcctgcctcc ccaacatggt ggtcatggct ccctccgacg aagcggagct    1140
catgaacatg atcgccaccg ccgccatcat cgacgaccga cctagctgcg tccggtaccc    1200
tagagggaac ggcatcggcg tcgctcttcc gtcgaacaac aaaggaactc cattagagat    1260
tggtaaggga agaatcttga aggaggggag caaagttgcg attctgggat tcggaaccat    1320
agtgcagaac tgcatggcgg cggcgaatct tctcgaacaa cacggaatct cagtaacagt    1380
agccgatgca agattctgca agccactcga tggggatttg ataaagaaac tggtgcagga    1440
gcatgaagta ctcatcactg ttgaagaagg atccatcggt ggattcagtg ctcacatttc    1500
tcatttcttg tccctcaatg gcttgctcga tggaaacctc aagtggaggc caatggttct    1560
```

-continued

```
tccagatagg tacattgatc atggagcaca gagtgatcaa atagaagaag cagggctgag    1620
tcctaagcat attgcaggga ctgttgtttc attgattgga ggaggaaagg acagtcttca    1680
tttgattaat aatttgtaat attattttaa tttatttctt cgaaaaggaa aagagaaaaa    1740
aatggagtct gaatttgagc agctgcaaaa attctccatg agagattagt gttaagatgt    1800
ataatgtaaa tatgggggaa ggtcaagact cttgacccat ggaaattggg ggagctgttc    1860
taaataattg ttgtgatggc agccttttct acatgtttta ttcaataaaa tcatttgtta    1920
cattttaaaa aaaaaaaaaa aaaaaaaaa                                      1949

<210> SEQ ID NO 2
<211> LENGTH: 216
<212> TYPE: DNA
<213> ORGANISM: Mentha piperita

<400> SEQUENCE: 2
gtcaactccc agctggttgg gagaaggctc ttcctacata caccccctgag agcccagccg    60 atgccacaag gaacctctct cagcaaaacc tcaacgctct agcaaaagtt ctcccaggtc   120
tgctaggagg cagcgctgac cttgcctcct ccaacatgac ccttctcaaa acattcggcg   180
acttccaaag tagcactccc gaagaacgaa atgtaa                             216

<210> SEQ ID NO 3
<211> LENGTH: 2500
<212> TYPE: DNA
<213> ORGANISM: Mentha piperita
<220> FEATURE:
<221> NAME/KEY: CDS
<222> LOCATION: (85)..(2247)

<400> SEQUENCE: 3
ctctctcaac acctctttcc tttcttcttc actagctact taatttagtt caagaaagaa    60
gagagagaaa gaagagagga agag atg gca tct tcc tgt gga gtt atc aag      111
                           Met Ala Ser Ser Cys Gly Val Ile Lys
                             1               5 agc agt ttc ttg cca tcg ctc cat tct gag gat tct acc ttc tta tca    159
Ser Ser Phe Leu Pro Ser Leu His Ser Glu Asp Ser Thr Phe Leu Ser
 10              15                  20                  25 cgt gct cct act tct ctt ccc ctc aaa aat cat aag tta aat gtg gta    207
Arg Ala Pro Thr Ser Leu Pro Leu Lys Asn His Lys Leu Asn Val Val
                 30                  35                  40 gca gct ctc caa caa gat agt tcg aac gac gtc gtt cct agc gga gac    255
Ala Ala Leu Gln Gln Asp Ser Ser Asn Asp Val Val Pro Ser Gly Asp
             45                  50                  55 agg ctg agc cgg ccg aaa tca aga gca ctg agt ttc acc gga gag aag    303
Arg Leu Ser Arg Pro Lys Ser Arg Ala Leu Ser Phe Thr Gly Glu Lys
         60                  65                  70 cct ccc att cct ata ctg gac acc atc aac tac cct aat cac atg aaa    351
Pro Pro Ile Pro Ile Leu Asp Thr Ile Asn Tyr Pro Asn His Met Lys
     75                  80                  85 aat ctt tcc gtc gag gaa ctc gca aac cta gct gat gaa ctg agg gaa    399
Asn Leu Ser Val Glu Glu Leu Ala Asn Leu Ala Asp Glu Leu Arg Glu
 90                  95                 100                 105 gag ata gtg tac acg gtg tcg aaa acc ggc ggc cat ctt agc tcg agc    447
Glu Ile Val Tyr Thr Val Ser Lys Thr Gly Gly His Leu Ser Ser Ser
                110                 115                 120 cta ggc gtg tcg gag ctc acc gtc gca ctt cat cac gtt ttc aac acg    495
Leu Gly Val Ser Glu Leu Thr Val Ala Leu His His Val Phe Asn Thr
            125                 130                 135
```

```
ccc gat gac aaa atc atc tgg gac gtc ggc cac cag gct tac cca cac    543
Pro Asp Asp Lys Ile Ile Trp Asp Val Gly His Gln Ala Tyr Pro His
        140                 145                 150 aaa atc ttg acc ggg aga aga gcg aga atg cac aca att agg cag aca    591
Lys Ile Leu Thr Gly Arg Arg Ala Arg Met His Thr Ile Arg Gln Thr
    155                 160                 165 ttt gga tta gca ggt ttc cct aag aga gat gaa agt gct cac gat gcc    639
Phe Gly Leu Ala Gly Phe Pro Lys Arg Asp Glu Ser Ala His Asp Ala
170                 175                 180                 185 ttc ggc gcc ggc cat agt tct acc agt att tct gct ggt tta ggg atg    687
Phe Gly Ala Gly His Ser Ser Thr Ser Ile Ser Ala Gly Leu Gly Met
                190                 195                 200 gcg gtg gcg aga gat tta ctg cag aag aac aac cac gtc ata tcg gtg    735
Ala Val Ala Arg Asp Leu Leu Gln Lys Asn Asn His Val Ile Ser Val
            205                 210                 215 atc ggc gac ggc gcc atg aca gct gga caa gcg tac gag gcc tta aac    783
Ile Gly Asp Gly Ala Met Thr Ala Gly Gln Ala Tyr Glu Ala Leu Asn
        220                 225                 230 aac gcc gga ttc ctc gat tcg aat ctc ata atc gtt tta aac gac aac    831
Asn Ala Gly Phe Leu Asp Ser Asn Leu Ile Ile Val Leu Asn Asp Asn
    235                 240                 245 aag cag gtg tct cta ccc acg gcc acc gtc gac ggc cct gcg ccg ccg    879
Lys Gln Val Ser Leu Pro Thr Ala Thr Val Asp Gly Pro Ala Pro Pro
250                 255                 260                 265 gtc gga gct ctg agc aaa gcc ctg acc aag ctg caa gcc agc aga aaa    927
Val Gly Ala Leu Ser Lys Ala Leu Thr Lys Leu Gln Ala Ser Arg Lys
                270                 275                 280 ttc cgg cag ctc cgc gaa gca gca aag agt atg act aag cag atg gga    975
Phe Arg Gln Leu Arg Glu Ala Ala Lys Ser Met Thr Lys Gln Met Gly
            285                 290                 295 gca ccg gca cat gaa ata gct tcg aag ttg aca caa tac gtg aaa ggg   1023
Ala Pro Ala His Glu Ile Ala Ser Lys Leu Thr Gln Tyr Val Lys Gly
        300                 305                 310 atg atg ggg aaa cca ggc gct tca ctt ttc gaa gaa ctg ggg att tat   1071
Met Met Gly Lys Pro Gly Ala Ser Leu Phe Glu Glu Leu Gly Ile Tyr
    315                 320                 325 tac atc gga cca gtc gac gtt gaa gat ctt gtt tat att ttc aag aaa   1119
Tyr Ile Gly Pro Val Asp Val Glu Asp Leu Val Tyr Ile Phe Lys Lys
330                 335                 340                 345 gtt aag gaa atg cct gcg cct ggg cct gtt ctt att cat atc atc acc   1167
Val Lys Glu Met Pro Ala Pro Gly Pro Val Leu Ile His Ile Ile Thr
                350                 355                 360 gaa aaa ggc aaa ggc tac ccc cct gca gaa att gct gcc gac aaa atg   1215
Glu Lys Gly Lys Gly Tyr Pro Pro Ala Glu Ile Ala Ala Asp Lys Met
            365                 370                 375 cat ggg gtg gtg aag ttt gat gcg aaa act ggg aaa cag atg aag acg   1263
His Gly Val Val Lys Phe Asp Ala Lys Thr Gly Lys Gln Met Lys Thr
        380                 385                 390 aag aac aag acg aag tca tac acc cag tac ttc gcc gag tct ctg gtg   1311
Lys Asn Lys Thr Lys Ser Tyr Thr Gln Tyr Phe Ala Glu Ser Leu Val
    395                 400                 405 gcg gag gcg gag cac gac gac aag atc gtg gcg atc cac gcc gcc atg   1359
Ala Glu Ala Glu His Asp Asp Lys Ile Val Ala Ile His Ala Ala Met
410                 415                 420                 425 ggg ggc ggc acc ggg ctc aac atc ttc cag aag cag ttc ccg gac cgg   1407
Gly Gly Gly Thr Gly Leu Asn Ile Phe Gln Lys Gln Phe Pro Asp Arg
                430                 435                 440 tgc ttc gac gtc ggg atc gcg gag cag cac gcg gtg acg ttc gcc gcc   1455
Cys Phe Asp Val Gly Ile Ala Glu Gln His Ala Val Thr Phe Ala Ala
            445                 450                 455
```

-continued

| | |
|---|---|
| ggt atg gcg gcg gag ggg ctg aag cct ttc tgc gcc atc tac tcc tcc<br>Gly Met Ala Ala Glu Gly Leu Lys Pro Phe Cys Ala Ile Tyr Ser Ser<br>460 465 470 | 1503 |
| ttc ctc cag agg ggc tac gac cag gtg gtc cac gac gtc gac ctc cag<br>Phe Leu Gln Arg Gly Tyr Asp Gln Val Val His Asp Val Asp Leu Gln<br>475 480 485 | 1551 |
| aag ctc ccg gtc cgg ttc atg atg gat cgg gca gga gtc gtc ggc gcc<br>Lys Leu Pro Val Arg Phe Met Met Asp Arg Ala Gly Val Val Gly Ala<br>490 495 500 505 | 1599 |
| gac ggc ccc acc cac tgc ggc gcc ttc gac acc acc tac atg gcc tgc<br>Asp Gly Pro Thr His Cys Gly Ala Phe Asp Thr Thr Tyr Met Ala Cys<br>510 515 520 | 1647 |
| ctc ccc aac atg gtg gtc atg gct ccc tcc gac gaa gcg gag ctc atg<br>Leu Pro Asn Met Val Val Met Ala Pro Ser Asp Glu Ala Glu Leu Met<br>525 530 535 | 1695 |
| aac atg atc gcc acc gcc gcc atc atc gac gac cga cct agc tgc gtc<br>Asn Met Ile Ala Thr Ala Ala Ile Ile Asp Asp Arg Pro Ser Cys Val<br>540 545 550 | 1743 |
| cgg tac cct aga ggg aac ggc atc ggc gtc gct ctt ccg tcg aac aac<br>Arg Tyr Pro Arg Gly Asn Gly Ile Gly Val Ala Leu Pro Ser Asn Asn<br>555 560 565 | 1791 |
| aaa gga act cca tta gag att ggt aag gga aga atc ttg aag gag ggg<br>Lys Gly Thr Pro Leu Glu Ile Gly Lys Gly Arg Ile Leu Lys Glu Gly<br>570 575 580 585 | 1839 |
| agc aaa gtt gcg att ctg gga ttc gga acc ata gtg cag aac tgc atg<br>Ser Lys Val Ala Ile Leu Gly Phe Gly Thr Ile Val Gln Asn Cys Met<br>590 595 600 | 1887 |
| gcg gcg gcg aat ctt ctc gaa caa cac gga atc tca gta aca gta gcc<br>Ala Ala Ala Asn Leu Leu Glu Gln His Gly Ile Ser Val Thr Val Ala<br>605 610 615 | 1935 |
| gat gca aga ttc tgc aag cca ctc gat ggg gat ttg ata aag aaa ctg<br>Asp Ala Arg Phe Cys Lys Pro Leu Asp Gly Asp Leu Ile Lys Lys Leu<br>620 625 630 | 1983 |
| gtg cag gag cat gaa gta ctc atc act gtt gaa gaa gga tcc atc ggt<br>Val Gln Glu His Glu Val Leu Ile Thr Val Glu Glu Gly Ser Ile Gly<br>635 640 645 | 2031 |
| gga ttc agt gct cac att tct cat ttc ttg tcc ctc aat ggc ttg ctc<br>Gly Phe Ser Ala His Ile Ser His Phe Leu Ser Leu Asn Gly Leu Leu<br>650 655 660 665 | 2079 |
| gat gga aac ctc aag tgg agg cca atg gtt ctt cca gat agg tac att<br>Asp Gly Asn Leu Lys Trp Arg Pro Met Val Leu Pro Asp Arg Tyr Ile<br>670 675 680 | 2127 |
| gat cat gga gca cag agt gat caa ata gaa gaa gca ggg ctg agt cct<br>Asp His Gly Ala Gln Ser Asp Gln Ile Glu Glu Ala Gly Leu Ser Pro<br>685 690 695 | 2175 |
| aag cat att gca ggg act gtt gtt tca ttg att gga gga gga aag gac<br>Lys His Ile Ala Gly Thr Val Val Ser Leu Ile Gly Gly Gly Lys Asp<br>700 705 710 | 2223 |
| agt ctt cat ttg att aat aat ttg taatattatt ttaatttatt tcttcgaaaa<br>Ser Leu His Leu Ile Asn Asn Leu<br>715 720 | 2277 |
| ggaaaagaga aaaaaatgga gtctgaattt gagcagctgc aaaaattctc catgagagat | 2337 |
| tagtgttaag atgtataatg taaatatggg ggaaggtcaa gactcttgac ccatggaaat | 2397 |
| tgggggagct gttctaaata attgttgtga tggcagcctt ttctacatgt tttattcaat | 2457 |
| aaaatcattt gttacatttt aaaaaaaaaa aaaaaaaaaa aaa | 2500 |

-continued

```
<210> SEQ ID NO 4
<211> LENGTH: 721
<212> TYPE: PRT
<213> ORGANISM: Mentha piperita

<400> SEQUENCE: 4

Met Ala Ser Ser Cys Gly Val Ile Lys Ser Ser Phe Leu Pro Ser Leu
  1               5                  10                  15

His Ser Glu Asp Ser Thr Phe Leu Ser Arg Ala Pro Thr Ser Leu Pro
             20                  25                  30

Leu Lys Asn His Lys Leu Asn Val Val Ala Ala Leu Gln Gln Asp Ser
         35                  40                  45

Ser Asn Asp Val Val Pro Ser Gly Asp Arg Leu Ser Arg Pro Lys Ser
     50                  55                  60

Arg Ala Leu Ser Phe Thr Gly Glu Lys Pro Pro Ile Pro Ile Leu Asp
 65                  70                  75                  80

Thr Ile Asn Tyr Pro Asn His Met Lys Asn Leu Ser Val Glu Glu Leu
                 85                  90                  95

Ala Asn Leu Ala Asp Glu Leu Arg Glu Glu Ile Val Tyr Thr Val Ser
            100                 105                 110

Lys Thr Gly Gly His Leu Ser Ser Ser Leu Gly Val Ser Glu Leu Thr
        115                 120                 125

Val Ala Leu His His Val Phe Asn Thr Pro Asp Asp Lys Ile Ile Trp
130                 135                 140

Asp Val Gly His Gln Ala Tyr Pro His Lys Ile Leu Thr Gly Arg Arg
145                 150                 155                 160

Ala Arg Met His Thr Ile Arg Gln Thr Phe Gly Leu Ala Gly Phe Pro
                165                 170                 175

Lys Arg Asp Glu Ser Ala His Asp Ala Phe Gly Ala Gly His Ser Ser
            180                 185                 190

Thr Ser Ile Ser Ala Gly Leu Gly Met Ala Val Ala Arg Asp Leu Leu
        195                 200                 205

Gln Lys Asn Asn His Val Ile Ser Val Ile Gly Asp Gly Ala Met Thr
    210                 215                 220

Ala Gly Gln Ala Tyr Glu Ala Leu Asn Asn Ala Gly Phe Leu Asp Ser
225                 230                 235                 240

Asn Leu Ile Ile Val Leu Asn Asp Asn Lys Gln Val Ser Leu Pro Thr
                245                 250                 255

Ala Thr Val Asp Gly Pro Ala Pro Pro Val Gly Ala Leu Ser Lys Ala
            260                 265                 270

Leu Thr Lys Leu Gln Ala Ser Arg Lys Phe Arg Gln Leu Arg Glu Ala
        275                 280                 285

Ala Lys Ser Met Thr Lys Gln Met Gly Ala Pro Ala His Glu Ile Ala
    290                 295                 300

Ser Lys Leu Thr Gln Tyr Val Lys Gly Met Met Gly Lys Pro Gly Ala
305                 310                 315                 320

Ser Leu Phe Glu Glu Leu Gly Ile Tyr Tyr Ile Gly Pro Val Asp Val
                325                 330                 335

Glu Asp Leu Val Tyr Ile Phe Lys Lys Val Lys Glu Met Pro Ala Pro
            340                 345                 350

Gly Pro Val Leu Ile His Ile Ile Thr Glu Lys Gly Lys Gly Tyr Pro
        355                 360                 365

Pro Ala Glu Ile Ala Ala Asp Lys Met His Gly Val Val Lys Phe Asp
    370                 375                 380
```

```
Ala Lys Thr Gly Lys Gln Met Lys Thr Lys Asn Lys Thr Lys Ser Tyr
385                 390                 395                 400

Thr Gln Tyr Phe Ala Glu Ser Leu Val Ala Glu Ala Glu His Asp Asp
            405                 410                 415

Lys Ile Val Ala Ile His Ala Ala Met Gly Gly Thr Gly Leu Asn
        420                 425                 430

Ile Phe Gln Lys Gln Phe Pro Asp Arg Cys Phe Asp Val Gly Ile Ala
            435                 440                 445

Glu Gln His Ala Val Thr Phe Ala Ala Gly Met Ala Ala Glu Gly Leu
    450                 455                 460

Lys Pro Phe Cys Ala Ile Tyr Ser Ser Phe Leu Gln Arg Gly Tyr Asp
465                 470                 475                 480

Gln Val Val His Asp Val Asp Leu Gln Lys Leu Pro Val Arg Phe Met
                485                 490                 495

Met Asp Arg Ala Gly Val Val Gly Ala Asp Gly Pro Thr His Cys Gly
            500                 505                 510

Ala Phe Asp Thr Thr Tyr Met Ala Cys Leu Pro Asn Met Val Val Met
        515                 520                 525

Ala Pro Ser Asp Glu Ala Glu Leu Met Asn Met Ile Ala Thr Ala Ala
530                 535                 540

Ile Ile Asp Asp Arg Pro Ser Cys Val Arg Tyr Pro Arg Gly Asn Gly
545                 550                 555                 560

Ile Gly Val Ala Leu Pro Ser Asn Asn Lys Gly Thr Pro Leu Glu Ile
            565                 570                 575

Gly Lys Gly Arg Ile Leu Lys Glu Gly Ser Lys Val Ala Ile Leu Gly
            580                 585                 590

Phe Gly Thr Ile Val Gln Asn Cys Met Ala Ala Ala Asn Leu Leu Glu
        595                 600                 605

Gln His Gly Ile Ser Val Thr Val Ala Asp Ala Arg Phe Cys Lys Pro
    610                 615                 620

Leu Asp Gly Asp Leu Ile Lys Lys Leu Val Gln Glu His Glu Val Leu
625                 630                 635                 640

Ile Thr Val Glu Glu Gly Ser Ile Gly Gly Phe Ser Ala His Ile Ser
            645                 650                 655

His Phe Leu Ser Leu Asn Gly Leu Leu Asp Gly Asn Leu Lys Trp Arg
        660                 665                 670

Pro Met Val Leu Pro Asp Arg Tyr Ile Asp His Gly Ala Gln Ser Asp
        675                 680                 685

Gln Ile Glu Glu Ala Gly Leu Ser Pro Lys His Ile Ala Gly Thr Val
    690                 695                 700

Val Ser Leu Ile Gly Gly Gly Lys Asp Ser Leu His Leu Ile Asn Asn
705                 710                 715                 720

Leu

<210> SEQ ID NO 5
<211> LENGTH: 2509
<212> TYPE: DNA
<213> ORGANISM: Mentha piperita
<220> FEATURE:
<221> NAME/KEY: CDS
<222> LOCATION: (85)..(2256)

<400> SEQUENCE: 5
ttctctctca acacctcttt cctttcttca ctagctactt aatttagttc aagaaagaaa      60
```

-continued

```
gagagagaaa aagagagga agag atg gca tct tcc tgt gga gtt atc aag    111
                    Met Ala Ser Ser Cys Gly Val Ile Lys
                     1               5 agc agt ttc ttg cca tcg ctc cat tct gag gat tct acc ttc tta tca  159
Ser Ser Phe Leu Pro Ser Leu His Ser Glu Asp Ser Thr Phe Leu Ser
 10              15                  20                  25 cgt gct cct act tct ctt ccc ctc aaa aat cat aag tta aat gtg gta  207
Arg Ala Pro Thr Ser Leu Pro Leu Lys Asn His Lys Leu Asn Val Val
                 30                  35                  40 gca gct ctc caa caa gat agt tcg aac gac gtc gtt cct agc gga gac  255
Ala Ala Leu Gln Gln Asp Ser Ser Asn Asp Val Val Pro Ser Gly Asp
             45                  50                  55 agg ctg agc cgg ccg aaa tca aga gca ctg agt ttc acc gga gag aag  303
Arg Leu Ser Arg Pro Lys Ser Arg Ala Leu Ser Phe Thr Gly Glu Lys
         60                  65                  70 cct ccc att cct ata ctg gac acc atc aac tac cct aat cac atg aaa  351
Pro Pro Ile Pro Ile Leu Asp Thr Ile Asn Tyr Pro Asn His Met Lys
 75                  80                  85 aat ctt tcc gtc gag gaa ctc gca aac cta gct gat gaa ctg agg gaa  399
Asn Leu Ser Val Glu Glu Leu Ala Asn Leu Ala Asp Glu Leu Arg Glu
 90                  95                 100                 105 gag ata gtg tac acg gtg tcg aaa acc ggc ggc cat ctt agc tcg agc  447
Glu Ile Val Tyr Thr Val Ser Lys Thr Gly Gly His Leu Ser Ser Ser
                110                 115                 120 cta ggc gtg tcg gag ctc acc gtc gca ctt cat cac gtt ttc aac acg  495
Leu Gly Val Ser Glu Leu Thr Val Ala Leu His His Val Phe Asn Thr
            125                 130                 135 ccc gat gac aaa atc atc tgg gac gtc ggc cac cag gct tac cca cac  543
Pro Asp Asp Lys Ile Ile Trp Asp Val Gly His Gln Ala Tyr Pro His
        140                 145                 150 aaa atc ttg acc ggg aga aga gcg aga atg cac aca att agg cag aca  591
Lys Ile Leu Thr Gly Arg Arg Ala Arg Met His Thr Ile Arg Gln Thr
    155                 160                 165 ttt gga tta gca ggt ttc cct aag aga gat gaa agt gct cac gat gcc  639
Phe Gly Leu Ala Gly Phe Pro Lys Arg Asp Glu Ser Ala His Asp Ala
170                 175                 180                 185 ttc ggc gcc ggc cat agt tct acc agt att tct gct ggt tta ggg atg  687
Phe Gly Ala Gly His Ser Ser Thr Ser Ile Ser Ala Gly Leu Gly Met
                190                 195                 200 gcg gtg gcg aga gat tta ctg cag aag aac aac cac gtc ata tcg gtg  735
Ala Val Ala Arg Asp Leu Leu Gln Lys Asn Asn His Val Ile Ser Val
            205                 210                 215 atc ggc gac ggc gcc atg aca gct gga caa gcg tac gag gcc tta aac  783
Ile Gly Asp Gly Ala Met Thr Ala Gly Gln Ala Tyr Glu Ala Leu Asn
        220                 225                 230 aac gcc gga ttc ctc gat tcg aat ctc ata atc gtt tta aac gac aac  831
Asn Ala Gly Phe Leu Asp Ser Asn Leu Ile Ile Val Leu Asn Asp Asn
    235                 240                 245 aag cag gtg tct cta ccc acg gcc acc gtc gac ggc cct gcg ccg ccg  879
Lys Gln Val Ser Leu Pro Thr Ala Thr Val Asp Gly Pro Ala Pro Pro
250                 255                 260                 265 gtc gga gct ctg agc aaa gcc ctg acc aag ctg caa gcc agc aga aaa  927
Val Gly Ala Leu Ser Lys Ala Leu Thr Lys Leu Gln Ala Ser Arg Lys
                270                 275                 280 ttc cgg cag ctc cgc gaa gca gca aag agt atg act aag cag atg gga  975
Phe Arg Gln Leu Arg Glu Ala Ala Lys Ser Met Thr Lys Gln Met Gly
            285                 290                 295 gca ccg gca cat gaa ata gct tcg aag ttg aca caa tac gtg aaa ggg 1023
Ala Pro Ala His Glu Ile Ala Ser Lys Leu Thr Gln Tyr Val Lys Gly
        300                 305                 310
```

```
atg atg ggg aaa cca ggc gct tca ctt ttc gaa gaa ctg ggg att tat        1071
Met Met Gly Lys Pro Gly Ala Ser Leu Phe Glu Glu Leu Gly Ile Tyr
    315                 320                 325 tac atc gga cca gtc gac ggc cat aac gtt gaa gat ctt gtt tat att        1119
Tyr Ile Gly Pro Val Asp Gly His Asn Val Glu Asp Leu Val Tyr Ile
330                 335                 340                 345 ttc aag aaa gtt aag gaa atg cct gcg cct ggg cct gtt ctt att cat        1167
Phe Lys Lys Val Lys Glu Met Pro Ala Pro Gly Pro Val Leu Ile His
            350                 355                 360 atc atc acc gaa aaa ggc aaa ggc tac ccc cct gca gaa att gct gcc        1215
Ile Ile Thr Glu Lys Gly Lys Gly Tyr Pro Pro Ala Glu Ile Ala Ala
        365                 370                 375 gac aaa atg cat ggg gtg gtg aag ttt gat gcg aaa act ggg aaa cag        1263
Asp Lys Met His Gly Val Val Lys Phe Asp Ala Lys Thr Gly Lys Gln
    380                 385                 390 atg aag acg aag aac aag acg aag tca tac acc cag tac ttc gcc gag        1311
Met Lys Thr Lys Asn Lys Thr Lys Ser Tyr Thr Gln Tyr Phe Ala Glu
395                 400                 405 tct ctg gtg gcg gag gcg gag cac gac gac aag atc gtg gcg atc cac        1359
Ser Leu Val Ala Glu Ala Glu His Asp Asp Lys Ile Val Ala Ile His
410                 415                 420                 425 gcc gcc atg ggg ggc ggc acc ggg ctc aac atc ttc cag aag cag ttc        1407
Ala Ala Met Gly Gly Gly Thr Gly Leu Asn Ile Phe Gln Lys Gln Phe
                430                 435                 440 ccg gac cgg tgc ttc gac gtc ggg atc gcg gag cag cac gcg gtg acg        1455
Pro Asp Arg Cys Phe Asp Val Gly Ile Ala Glu Gln His Ala Val Thr
            445                 450                 455 ttc gcc gcc ggt atg gcg gcg gag ggg ctg aag cct ttc tgc gcc atc        1503
Phe Ala Ala Gly Met Ala Ala Glu Gly Leu Lys Pro Phe Cys Ala Ile
        460                 465                 470 tac tcc tcc ttc ctc cag agg ggc tac gac cag gtg gtc cac gac gtc        1551
Tyr Ser Ser Phe Leu Gln Arg Gly Tyr Asp Gln Val Val His Asp Val
    475                 480                 485 gac ctc cag aag ctc ccg gtc cgg ttc atg atg gat cgg gca gga gtc        1599
Asp Leu Gln Lys Leu Pro Val Arg Phe Met Met Asp Arg Ala Gly Val
490                 495                 500                 505 gtc ggc gcc gac ggc ccc acc cac tgc ggc gcc ttc gac acc acc tac        1647
Val Gly Ala Asp Gly Pro Thr His Cys Gly Ala Phe Asp Thr Thr Tyr
                510                 515                 520 atg gcc tgc ctc ccc aac atg gtg gtc atg gct ccc tcc gac gaa gcg        1695
Met Ala Cys Leu Pro Asn Met Val Val Met Ala Pro Ser Asp Glu Ala
            525                 530                 535 gag ctc atg aac atg atc gcc acc gcc gcc atc atc gac gac cga cct        1743
Glu Leu Met Asn Met Ile Ala Thr Ala Ala Ile Ile Asp Asp Arg Pro
        540                 545                 550 agc tgc gtc cgg tac cct aga ggg aac ggc atc ggc gtc gct ctt ccg        1791
Ser Cys Val Arg Tyr Pro Arg Gly Asn Gly Ile Gly Val Ala Leu Pro
    555                 560                 565 tcg aac aac aaa gga act cca tta gag att ggt aag gga aga atc ttg        1839
Ser Asn Asn Lys Gly Thr Pro Leu Glu Ile Gly Lys Gly Arg Ile Leu
570                 575                 580                 585 aag gag ggg agc aaa gtt gcg att ctg gga ttc gga acc ata gtg cag        1887
Lys Glu Gly Ser Lys Val Ala Ile Leu Gly Phe Gly Thr Ile Val Gln
                590                 595                 600 aac tgc atg gcg gcg gcg aat ctt ctc gaa caa cac gga atc tca gta        1935
Asn Cys Met Ala Ala Ala Asn Leu Leu Glu Gln His Gly Ile Ser Val
            605                 610                 615 aca gta gcc gat gca aga ttc tgc aag cca ctc gat ggg gat ttg ata        1983
Thr Val Ala Asp Ala Arg Phe Cys Lys Pro Leu Asp Gly Asp Leu Ile
        620                 625                 630
```

| | | | | | | | | | | | | | | | | |
|---|---|---|---|---|---|---|---|---|---|---|---|---|---|---|---|---|
| aag | aaa | ctg | gtg | cag | gag | cat | gaa | gta | ctc | atc | act | gtt | gaa | gaa | gga | 2031 |
| Lys | Lys | Leu | Val | Gln | Glu | His | Glu | Val | Leu | Ile | Thr | Val | Glu | Glu | Gly | |
| | 635 | | | | 640 | | | | | 645 | | | | | | |
| tcc | atc | ggt | gga | ttc | agt | gct | cac | att | tct | cat | ttc | ttg | tcc | ctc | aat | 2079 |
| Ser | Ile | Gly | Gly | Phe | Ser | Ala | His | Ile | Ser | His | Phe | Leu | Ser | Leu | Asn | |
| 650 | | | | | 655 | | | | | 660 | | | | | 665 | |
| ggc | ttg | ctc | gat | gga | aac | ctc | aag | tgg | agg | cca | atg | gtt | ctt | cca | gat | 2127 |
| Gly | Leu | Leu | Asp | Gly | Asn | Leu | Lys | Trp | Arg | Pro | Met | Val | Leu | Pro | Asp | |
| | | | | 670 | | | | | 675 | | | | | 680 | | |
| agg | tac | att | gat | cat | gga | gca | cag | agt | gat | caa | ata | gaa | gaa | gca | ggg | 2175 |
| Arg | Tyr | Ile | Asp | His | Gly | Ala | Gln | Ser | Asp | Gln | Ile | Glu | Glu | Ala | Gly | |
| | | | | 685 | | | | | 690 | | | | | 695 | | |
| ctg | agt | cct | aag | cat | att | gca | ggg | act | gtt | gtt | tca | ttg | att | gga | gga | 2223 |
| Leu | Ser | Pro | Lys | His | Ile | Ala | Gly | Thr | Val | Val | Ser | Leu | Ile | Gly | Gly | |
| | | 700 | | | | | 705 | | | | | 710 | | | | |
| gga | aag | gac | agt | ctt | cat | ttg | att | aat | aat | ttg | taatattatt | | ttaatttatt | | | 2276 |
| Gly | Lys | Asp | Ser | Leu | His | Leu | Ile | Asn | Asn | Leu | | | | | | |
| | 715 | | | | 720 | | | | | | | | | | | | tcttcgaaaa ggaaaagaga aaaaaatgga gtctgaattt gagcagctgc aaaaattctc 2336 catgagagat tagtgttaag atgtataatg taaatatggg ggaaggtcaa gactcttgac 2396 ccatggaaat tgggggagct gttctaaata attgttgtga tggcagcctt ttctacatgt 2456 tttattcaat aaaatcattt gttacatttt aaaaaaaaaa aaaaaaaaaa aaa 2509

<210> SEQ ID NO 6
<211> LENGTH: 724
<212> TYPE: PRT
<213> ORGANISM: Mentha piperita

<400> SEQUENCE: 6

Met Ala Ser Ser Cys Gly Val Ile Lys Ser Ser Phe Leu Pro Ser Leu
 1               5                  10                  15

His Ser Glu Asp Ser Thr Phe Leu Ser Arg Ala Pro Thr Ser Leu Pro
             20                  25                  30

Leu Lys Asn His Lys Leu Asn Val Val Ala Ala Leu Gln Gln Asp Ser
         35                  40                  45

Ser Asn Asp Val Val Pro Ser Gly Asp Arg Leu Ser Arg Pro Lys Ser
     50                  55                  60

Arg Ala Leu Ser Phe Thr Gly Glu Lys Pro Pro Ile Pro Ile Leu Asp
 65                  70                  75                  80

Thr Ile Asn Tyr Pro Asn His Met Lys Asn Leu Ser Val Glu Glu Leu
                 85                  90                  95

Ala Asn Leu Ala Asp Glu Leu Arg Glu Glu Ile Val Tyr Thr Val Ser
            100                 105                 110

Lys Thr Gly Gly His Leu Ser Ser Ser Leu Gly Val Ser Glu Leu Thr
        115                 120                 125

Val Ala Leu His His Val Phe Asn Thr Pro Asp Asp Lys Ile Ile Trp
    130                 135                 140

Asp Val Gly His Gln Ala Tyr Pro His Lys Ile Leu Thr Gly Arg Arg
145                 150                 155                 160

Ala Arg Met His Thr Ile Arg Gln Thr Phe Gly Leu Ala Gly Phe Pro
                165                 170                 175

Lys Arg Asp Glu Ser Ala His Asp Ala Phe Gly Ala Gly His Ser Ser
            180                 185                 190

Thr Ser Ile Ser Ala Gly Leu Gly Met Ala Val Ala Arg Asp Leu Leu
        195                 200                 205

-continued

```
Gln Lys Asn Asn His Val Ile Ser Val Ile Gly Asp Gly Ala Met Thr
    210                 215                 220

Ala Gly Gln Ala Tyr Glu Ala Leu Asn Asn Ala Gly Phe Leu Asp Ser
225                 230                 235                 240

Asn Leu Ile Ile Val Leu Asn Asp Asn Lys Gln Val Ser Leu Pro Thr
                245                 250                 255

Ala Thr Val Asp Gly Pro Ala Pro Val Gly Ala Leu Ser Lys Ala
            260                 265                 270

Leu Thr Lys Leu Gln Ala Ser Arg Lys Phe Arg Gln Leu Arg Glu Ala
        275                 280                 285

Ala Lys Ser Met Thr Lys Gln Met Gly Ala Pro Ala His Glu Ile Ala
    290                 295                 300

Ser Lys Leu Thr Gln Tyr Val Lys Gly Met Met Gly Lys Pro Gly Ala
305                 310                 315                 320

Ser Leu Phe Glu Glu Leu Gly Ile Tyr Tyr Ile Gly Pro Val Asp Gly
                325                 330                 335

His Asn Val Glu Asp Leu Val Tyr Ile Phe Lys Lys Val Lys Glu Met
            340                 345                 350

Pro Ala Pro Gly Pro Val Leu Ile His Ile Ile Thr Glu Lys Gly Lys
        355                 360                 365

Gly Tyr Pro Pro Ala Glu Ile Ala Ala Asp Lys Met His Gly Val Val
    370                 375                 380

Lys Phe Asp Ala Lys Thr Gly Lys Gln Met Lys Thr Lys Asn Lys Thr
385                 390                 395                 400

Lys Ser Tyr Thr Gln Tyr Phe Ala Glu Ser Leu Val Ala Glu Ala Glu
                405                 410                 415

His Asp Asp Lys Ile Val Ala Ile His Ala Ala Met Gly Gly Gly Thr
            420                 425                 430

Gly Leu Asn Ile Phe Gln Lys Gln Phe Pro Asp Arg Cys Phe Asp Val
        435                 440                 445

Gly Ile Ala Glu Gln His Ala Val Thr Phe Ala Ala Gly Met Ala Ala
    450                 455                 460

Glu Gly Leu Lys Pro Phe Cys Ala Ile Tyr Ser Ser Phe Leu Gln Arg
465                 470                 475                 480

Gly Tyr Asp Gln Val Val His Asp Val Asp Leu Gln Lys Leu Pro Val
                485                 490                 495

Arg Phe Met Met Asp Arg Ala Gly Val Val Gly Ala Asp Gly Pro Thr
            500                 505                 510

His Cys Gly Ala Phe Asp Thr Thr Tyr Met Ala Cys Leu Pro Asn Met
        515                 520                 525

Val Val Met Ala Pro Ser Asp Glu Ala Glu Leu Met Asn Met Ile Ala
    530                 535                 540

Thr Ala Ala Ile Ile Asp Asp Arg Pro Ser Cys Val Arg Tyr Pro Arg
545                 550                 555                 560

Gly Asn Gly Ile Gly Val Ala Leu Pro Ser Asn Asn Lys Gly Thr Pro
                565                 570                 575

Leu Glu Ile Gly Lys Gly Arg Ile Leu Lys Glu Gly Ser Lys Val Ala
            580                 585                 590

Ile Leu Gly Phe Gly Thr Ile Val Gln Asn Cys Met Ala Ala Ala Asn
        595                 600                 605

Leu Leu Glu Gln His Gly Ile Ser Val Thr Val Ala Asp Ala Arg Phe
    610                 615                 620
```

```
Cys Lys Pro Leu Asp Gly Asp Leu Ile Lys Lys Leu Val Gln Glu His
625                 630                 635                 640

Glu Val Leu Ile Thr Val Glu Gly Ser Ile Gly Gly Phe Ser Ala
            645                 650                 655

His Ile Ser His Phe Leu Ser Leu Asn Gly Leu Leu Asp Gly Asn Leu
            660                 665                 670

Lys Trp Arg Pro Met Val Leu Pro Asp Arg Tyr Ile Asp His Gly Ala
            675                 680                 685

Gln Ser Asp Gln Ile Glu Glu Ala Gly Leu Ser Pro Lys His Ile Ala
            690                 695                 700

Gly Thr Val Val Ser Leu Ile Gly Gly Lys Asp Ser Leu His Leu
705                 710                 715                 720

Ile Asn Asn Leu

<210> SEQ ID NO 7
<211> LENGTH: 2561
<212> TYPE: DNA
<213> ORGANISM: Mentha piperita
<220> FEATURE:
<221> NAME/KEY: CDS
<222> LOCATION: (128)..(2308)

<400> SEQUENCE: 7
```

| | |
|---|---|
| ctttctctct caacacttct ttcctttctt cactagctac ttaatttagt ccaagaaaga | 60 |
| aagagaaaga gagagagaga gagagagaga gagaggagga gagagagaga gagagagaga | 120 |

```
gagagag atg gca tct tcc tgt gga gtt atc aag agc agt ttc ttg cca    169
        Met Ala Ser Ser Cys Gly Val Ile Lys Ser Ser Phe Leu Pro
          1               5                  10 tcg ctc cat tct gag gat tct acc ttc tta tca cgt gct cct act tct    217
Ser Leu His Ser Glu Asp Ser Thr Phe Leu Ser Arg Ala Pro Thr Ser
 15              20                  25                  30 ctt ccc ctc aaa aat cat aag tta aat gtg gta gca gct ctc caa caa    265
Leu Pro Leu Lys Asn His Lys Leu Asn Val Val Ala Ala Leu Gln Gln
             35                  40                  45 gat agt tcg aac gac gac gtc gtt cct agc gga gac agg ctg agc cgg    313
Asp Ser Ser Asn Asp Asp Val Val Pro Ser Gly Asp Arg Leu Ser Arg
         50                  55                  60 ccg aaa tca aga gca ctg agt ttc acc gga gag aag cct ccc att cct    361
Pro Lys Ser Arg Ala Leu Ser Phe Thr Gly Glu Lys Pro Pro Ile Pro
     65                  70                  75 ata ctg gac acc atc aac tac cct aat cac atg aaa aat ctt tcc gtc    409
Ile Leu Asp Thr Ile Asn Tyr Pro Asn His Met Lys Asn Leu Ser Val
 80                  85                  90 gag gaa ctc gca aac cta gct gat gaa ctg agg gaa gag ata gtg tac    457
Glu Glu Leu Ala Asn Leu Ala Asp Glu Leu Arg Glu Glu Ile Val Tyr
 95                 100                 105                 110 acg gtg tcg aaa acc ggc ggc cat ctt agc tcg agc cta ggc gtg tcg    505
Thr Val Ser Lys Thr Gly Gly His Leu Ser Ser Ser Leu Gly Val Ser
                115                 120                 125 gag ctc acc gtc gca ctt cat cac gtt ttc aac acg ccc gat gac aaa    553
Glu Leu Thr Val Ala Leu His His Val Phe Asn Thr Pro Asp Asp Lys
            130                 135                 140 atc atc tgg gac gtc ggc cac cag gct tac cca cac aaa atc ttg acc    601
Ile Ile Trp Asp Val Gly His Gln Ala Tyr Pro His Lys Ile Leu Thr
        145                 150                 155 ggg aga aga gcg aga atg cac aca att agg cag aca ttt gga tta gca    649
Gly Arg Arg Ala Arg Met His Thr Ile Arg Gln Thr Phe Gly Leu Ala
    160                 165                 170
```

-continued

| | | |
|---|---|---|
| ggt ttc cct aag aga gat gaa agt gct cac gat gcc ttc ggc gcc ggc<br>Gly Phe Pro Lys Arg Asp Glu Ser Ala His Asp Ala Phe Gly Ala Gly<br>175                         180                     185                  190 | 697 |
| cat agt tct acc agt att tct gct ggt tta ggg atg gcg gtg gcg aga<br>His Ser Ser Thr Ser Ile Ser Ala Gly Leu Gly Met Ala Val Ala Arg<br>                      195                        200                     205 | 745 |
| gat tta ctg cag aag aac aac cac gtc ata tcg gtg atc ggc gac ggc<br>Asp Leu Leu Gln Lys Asn Asn His Val Ile Ser Val Ile Gly Asp Gly<br>          210                     215                     220 | 793 |
| gcc atg aca gct gga caa gcg tac gag gcc tta aac aac gcc gga ttc<br>Ala Met Thr Ala Gly Gln Ala Tyr Glu Ala Leu Asn Asn Ala Gly Phe<br>              225                     230                     235 | 841 |
| ctc gat tcg aat ctc ata atc gtt tta aac gac aac aag cag gtg tct<br>Leu Asp Ser Asn Leu Ile Ile Val Leu Asn Asp Asn Lys Gln Val Ser<br>240                         245                     250 | 889 |
| cta ccc acg gcc acc gtc gac ggc cct gcg ccg ccg gtc gga gct ctg<br>Leu Pro Thr Ala Thr Val Asp Gly Pro Ala Pro Pro Val Gly Ala Leu<br>255                         260                     265                  270 | 937 |
| agc aaa gcc ctg acc aag ctg caa gcc agc aga aaa ttc cgg cag ctc<br>Ser Lys Ala Leu Thr Lys Leu Gln Ala Ser Arg Lys Phe Arg Gln Leu<br>              275                     280                     285 | 985 |
| cgc gaa gca gca aag agt atg act aag cag atg gga gca ccg gca cat<br>Arg Glu Ala Ala Lys Ser Met Thr Lys Gln Met Gly Ala Pro Ala His<br>          290                     295                     300 | 1033 |
| gaa ata gct tcg aag ttg aca caa tac gtg aaa ggg atg atg ggg aaa<br>Glu Ile Ala Ser Lys Leu Thr Gln Tyr Val Lys Gly Met Met Gly Lys<br>305                         310                     315 | 1081 |
| cca ggc gct tca ctt ttc gaa gaa ctg ggg att tat tac atc gga cca<br>Pro Gly Ala Ser Leu Phe Glu Glu Leu Gly Ile Tyr Tyr Ile Gly Pro<br>320                         325                     330 | 1129 |
| gtc gac ggc cat aac gtt gaa gat ctt gtt tat att ttc aag aaa gtt<br>Val Asp Gly His Asn Val Glu Asp Leu Val Tyr Ile Phe Lys Lys Val<br>335                         340                     345                  350 | 1177 |
| aag gaa atg cct gcg cct ggg cct gtt ctt att cat atc atc acc gaa<br>Lys Glu Met Pro Ala Pro Gly Pro Val Leu Ile His Ile Ile Thr Glu<br>              355                     360                     365 | 1225 |
| aaa ggc aaa ggc tac ccc cct gca gaa att gct gcc gac aaa atg cat<br>Lys Gly Lys Gly Tyr Pro Pro Ala Glu Ile Ala Ala Asp Lys Met His<br>          370                     375                     380 | 1273 |
| ggg gtg gtg aag ttt gat gcg aaa act ggg aaa cag atg aag acg aag<br>Gly Val Val Lys Phe Asp Ala Lys Thr Gly Lys Gln Met Lys Thr Lys<br>              385                     390                     395 | 1321 |
| aac aag acg aag tca tac acc cag tac ttc gcc gag tct ctg gtg gcg<br>Asn Lys Thr Lys Ser Tyr Thr Gln Tyr Phe Ala Glu Ser Leu Val Ala<br>400                         405                     410 | 1369 |
| gag gcg gag cac gac gac aag atc gtg gcg atc cac gcc gcc atg ggg<br>Glu Ala Glu His Asp Asp Lys Ile Val Ala Ile His Ala Ala Met Gly<br>415                         420                     425                  430 | 1417 |
| ggc ggc acc ggg ctc aac atc ttc cag aag cag ttc ccg gac cgg tgc<br>Gly Gly Thr Gly Leu Asn Ile Phe Gln Lys Gln Phe Pro Asp Arg Cys<br>              435                     440                     445 | 1465 |
| ttc gac gtc ggg atc gcg gag cag cac gcg gtg acg ttc gcc gcc ggt<br>Phe Asp Val Gly Ile Ala Glu Gln His Ala Val Thr Phe Ala Ala Gly<br>          450                     455                     460 | 1513 |
| atg gcg gcg gag ggg ctg aag cct ttc tgc gcc atc tac tcc tcc ttc<br>Met Ala Ala Glu Gly Leu Lys Pro Phe Cys Ala Ile Tyr Ser Ser Phe<br>              465                     470                     475 | 1561 |
| ctc cag agg ggc tac gac cag gtg gtc cac gac gtc gac ctc cag aag<br>Leu Gln Arg Gly Tyr Asp Gln Val Val His Asp Val Asp Leu Gln Lys<br>          480                     485                     490 | 1609 |

-continued

```
ctc ccg gtc cgg ttc atg atg gat cgg gca gga gtc gtc ggc gcc gac      1657
Leu Pro Val Arg Phe Met Met Asp Arg Ala Gly Val Val Gly Ala Asp
495                 500                 505                 510 ggc ccc acc cac tgc ggc gcc ttc gac acc acc tac atg gcc tgc ctc      1705
Gly Pro Thr His Cys Gly Ala Phe Asp Thr Thr Tyr Met Ala Cys Leu
                515                 520                 525 ccc aac atg gtg gtc atg gct ccc tcc gac gaa gcg gag ctc atg aac      1753
Pro Asn Met Val Val Met Ala Pro Ser Asp Glu Ala Glu Leu Met Asn
        530                 535                 540 atg atc gcc acc gcc gcc atc atc gac gac cga cct agc tgc gtc cgg      1801
Met Ile Ala Thr Ala Ala Ile Ile Asp Asp Arg Pro Ser Cys Val Arg
    545                 550                 555 tac cct aga ggg aac ggc atc ggc gtc gct ctt ccg tcg aac aac aaa      1849
Tyr Pro Arg Gly Asn Gly Ile Gly Val Ala Leu Pro Ser Asn Asn Lys
560                 565                 570 gga act cca tta gag att ggt aag gga aga atc ttg aag gag ggg agc      1897
Gly Thr Pro Leu Glu Ile Gly Lys Gly Arg Ile Leu Lys Glu Gly Ser
575                 580                 585                 590 aaa gtt gcg att ctg gga ttc gga acc ata gtg cag aac tgc atg gcg      1945
Lys Val Ala Ile Leu Gly Phe Gly Thr Ile Val Gln Asn Cys Met Ala
                595                 600                 605 gcg gcg aat ctt ctc gaa caa cac gga atc tca gta aca gta gcc gat      1993
Ala Ala Asn Leu Leu Glu Gln His Gly Ile Ser Val Thr Val Ala Asp
        610                 615                 620 gca aga ttc tgc aag cca ctc gat ggg gat ttg ata aag aaa ctg gtg      2041
Ala Arg Phe Cys Lys Pro Leu Asp Gly Asp Leu Ile Lys Lys Leu Val
    625                 630                 635 cag gag cat gaa gta ctc atc act gtt gaa gaa gga tcc atc ggg atc      2089
Gln Glu His Glu Val Leu Ile Thr Val Glu Glu Gly Ser Ile Gly Ile
640                 645                 650 ggt gga ttc agt gct cac att tct cat ttc ttg tcc ctc aat ggc ttg      2137
Gly Gly Phe Ser Ala His Ile Ser His Phe Leu Ser Leu Asn Gly Leu
655                 660                 665                 670 ctc gat gga aac ctc aag tgg agg cca atg gtt ctt cca gat agg tac      2185
Leu Asp Gly Asn Leu Lys Trp Arg Pro Met Val Leu Pro Asp Arg Tyr
                675                 680                 685 att gat cat gga gca cag agt gat caa ata gaa gaa gca ggg ctg agt      2233
Ile Asp His Gly Ala Gln Ser Asp Gln Ile Glu Glu Ala Gly Leu Ser
        690                 695                 700 cct aag cat att gca ggg act gtt gtt tca ttg att gga gga gga aag      2281
Pro Lys His Ile Ala Gly Thr Val Val Ser Leu Ile Gly Gly Gly Lys
    705                 710                 715 gac agt ctt cat ttg att aat aat ttg taatattatt ttaatttatt            2328
Asp Ser Leu His Leu Ile Asn Asn Leu
    720                 725 tcttcgaaaa ggaaaagaga aaaaaatgga gtctgaattt gagcagctgc aaaaattctc    2388
catgagagat tagtgttaag atgtataatg taaatatggg ggaaggtcaa gactcttgac    2448
ccatggaaat tgggggagct gttctaaata attgttgtga tggcagcctt ttctacatgt    2508
tttattcaat aaaatcattt gttacatttt aaaaaaaaaa aaaaaaaaaa aaa           2561

<210> SEQ ID NO 8
<211> LENGTH: 727
<212> TYPE: PRT
<213> ORGANISM: Mentha piperita

<400> SEQUENCE: 8

Met Ala Ser Ser Cys Gly Val Ile Lys Ser Ser Phe Leu Pro Ser Leu
 1               5                  10                  15
```

-continued

```
His Ser Glu Asp Ser Thr Phe Leu Ser Arg Ala Pro Thr Ser Leu Pro
         20                  25                  30
Leu Lys Asn His Lys Leu Asn Val Val Ala Leu Gln Gln Asp Ser
         35                  40                  45
Ser Asn Asp Asp Val Val Pro Ser Gly Asp Arg Leu Ser Arg Pro Lys
         50                  55                  60
Ser Arg Ala Leu Ser Phe Thr Gly Glu Lys Pro Pro Ile Pro Ile Leu
 65                  70                  75                  80
Asp Thr Ile Asn Tyr Pro Asn His Met Lys Asn Leu Ser Val Glu Glu
                 85                  90                  95
Leu Ala Asn Leu Ala Asp Glu Leu Arg Glu Glu Ile Val Tyr Thr Val
                100                 105                 110
Ser Lys Thr Gly Gly His Leu Ser Ser Leu Gly Val Ser Glu Leu
         115                 120                 125
Thr Val Ala Leu His His Val Phe Asn Thr Pro Asp Asp Lys Ile Ile
         130                 135                 140
Trp Asp Val Gly His Gln Ala Tyr Pro His Lys Ile Leu Thr Gly Arg
145                 150                 155                 160
Arg Ala Arg Met His Thr Ile Arg Gln Thr Phe Gly Leu Ala Gly Phe
                 165                 170                 175
Pro Lys Arg Asp Glu Ser Ala His Asp Ala Phe Gly Ala Gly His Ser
                 180                 185                 190
Ser Thr Ser Ile Ser Ala Gly Leu Gly Met Ala Val Ala Arg Asp Leu
         195                 200                 205
Leu Gln Lys Asn Asn His Val Ile Ser Val Ile Gly Asp Gly Ala Met
         210                 215                 220
Thr Ala Gly Gln Ala Tyr Glu Ala Leu Asn Asn Ala Gly Phe Leu Asp
225                 230                 235                 240
Ser Asn Leu Ile Ile Val Leu Asn Asp Asn Lys Gln Val Ser Leu Pro
                 245                 250                 255
Thr Ala Thr Val Asp Gly Pro Ala Pro Pro Val Gly Ala Leu Ser Lys
                 260                 265                 270
Ala Leu Thr Lys Leu Gln Ala Ser Arg Lys Phe Arg Gln Leu Arg Glu
         275                 280                 285
Ala Ala Lys Ser Met Thr Lys Gln Met Gly Ala Pro Ala His Glu Ile
         290                 295                 300
Ala Ser Lys Leu Thr Gln Tyr Val Lys Gly Met Met Gly Lys Pro Gly
305                 310                 315                 320
Ala Ser Leu Phe Glu Glu Leu Gly Ile Tyr Tyr Ile Gly Pro Val Asp
                 325                 330                 335
Gly His Asn Val Glu Asp Leu Val Tyr Ile Phe Lys Lys Val Lys Glu
                 340                 345                 350
Met Pro Ala Pro Gly Pro Val Leu Ile His Ile Ile Thr Glu Lys Gly
         355                 360                 365
Lys Gly Tyr Pro Pro Ala Glu Ile Ala Ala Asp Lys Met His Gly Val
         370                 375                 380
Val Lys Phe Asp Ala Lys Thr Gly Lys Gln Met Lys Thr Lys Asn Lys
385                 390                 395                 400
Thr Lys Ser Tyr Thr Gln Tyr Phe Ala Glu Ser Leu Val Ala Glu Ala
                 405                 410                 415
Glu His Asp Asp Lys Ile Val Ala Ile His Ala Ala Met Gly Gly Gly
                 420                 425                 430
```

```
Thr Gly Leu Asn Ile Phe Gln Lys Gln Phe Pro Asp Arg Cys Phe Asp
        435                 440                 445

Val Gly Ile Ala Glu Gln His Ala Val Thr Phe Ala Ala Gly Met Ala
        450                 455                 460

Ala Glu Gly Leu Lys Pro Phe Cys Ala Ile Tyr Ser Ser Phe Leu Gln
465                 470                 475                 480

Arg Gly Tyr Asp Gln Val Val His Val Asp Leu Gln Lys Leu Pro
                485                 490                 495

Val Arg Phe Met Met Asp Arg Ala Gly Val Val Gly Ala Asp Gly Pro
                500                 505                 510

Thr His Cys Gly Ala Phe Asp Thr Thr Tyr Met Ala Cys Leu Pro Asn
            515                 520                 525

Met Val Val Met Ala Pro Ser Asp Glu Ala Glu Leu Met Asn Met Ile
        530                 535                 540

Ala Thr Ala Ala Ile Ile Asp Asp Arg Pro Ser Cys Val Arg Tyr Pro
545                 550                 555                 560

Arg Gly Asn Gly Ile Gly Val Ala Leu Pro Ser Asn Asn Lys Gly Thr
                565                 570                 575

Pro Leu Glu Ile Gly Lys Gly Arg Ile Leu Lys Glu Gly Ser Lys Val
                580                 585                 590

Ala Ile Leu Gly Phe Gly Thr Ile Val Gln Asn Cys Met Ala Ala Ala
            595                 600                 605

Asn Leu Leu Glu Gln His Gly Ile Ser Val Thr Val Ala Asp Ala Arg
        610                 615                 620

Phe Cys Lys Pro Leu Asp Gly Asp Leu Ile Lys Lys Leu Val Gln Glu
625                 630                 635                 640

His Glu Val Leu Ile Thr Val Glu Glu Gly Ser Ile Gly Ile Gly Gly
                645                 650                 655

Phe Ser Ala His Ile Ser His Phe Leu Ser Leu Asn Gly Leu Leu Asp
            660                 665                 670

Gly Asn Leu Lys Trp Arg Pro Met Val Leu Pro Asp Arg Tyr Ile Asp
        675                 680                 685

His Gly Ala Gln Ser Asp Gln Ile Glu Glu Ala Gly Leu Ser Pro Lys
        690                 695                 700

His Ile Ala Gly Thr Val Val Ser Leu Ile Gly Gly Gly Lys Asp Ser
705                 710                 715                 720

Leu His Leu Ile Asn Asn Leu
                725

<210> SEQ ID NO 9
<211> LENGTH: 617
<212> TYPE: DNA
<213> ORGANISM: Mentha piperita

<400> SEQUENCE: 9
aagagcgaga atgcacacaa ttaggcagac atttggatta gcaggtttcc ctaagagaga      60
tgaaagtgct cacgatgcct tcggcgccgg ccatagttct accagtattt ctgctggttt     120
agggatggcg gtggcgagag atttactgca gaagaacaac cacgtcatat cggtgatcgg     180
cgacggcgcc atgacagctg acaagcgta cgaggcctta acaacgccg gattcctcga      240 ttcgaatctc ataatcgttt taaacgacaa caagcaggtg tctctaccca cggccaccgt     300
cgacggccct gcgccgccgg tcggagctct gagcaaagcc ctgaccaagc tgcaagccag     360
cagaaaattc cggcagctcc gcgaagcagc aaagagtatg actaagcaga tgggagcacc     420
```

```
ggcacatgaa atagcttcga agttgacaca atacgtgaaa gggatgatgg ggaaaccagg    480
cgcttcactt ttcgaagaac tggggattta ttacatcgga ccagtcgacg gccataacgt    540
tgaagatctt gtttatattt tcaagaaagt taaggaaatg cctgcgcctg ggcctgttct    600
tattcatatc atcaccg                                                   617
```

```
<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: consensus
      transketolase motif wherein Xaa at position 4 represents a
      sequence of 7 to 8 amino acids, Xaa at position 6 represents a
      sequence of 3 to 4 amino acids, and Xaa at position 8 represents a
      sequence of 11 to 13 amino acids
<220> FEATURE:
<221> NAME/KEY: DOMAIN
<222> LOCATION: (1)..(10)

<400> SEQUENCE: 10
```

Gly Asp Gly Xaa Glu Xaa Ala Xaa Asn Asn
 1               5                  10

```
<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence:
      transketolase motif from Mentha piperita wherein Xaa at position 3
      represents Ala or Ser Xaa at position 4 represents any amino acid,
      Xaa at position 6 represents Ala or Gly, Xaa at position 8
      represents Gln or Met, Xaa at position 10 represents any amino
      acid, Xaa at position 13 represents any amino acid, Xaa at
      position 15 represents Asn or His, Xaa at position 18 represents a
      sequence 7 to 8 amino acids, Xaa at position 19 represents Ile or
      Val and Xaa at position 20 represents Ile or Val
<220> FEATURE:
<221> NAME/KEY: DOMAIN
<222> LOCATION: (1)..(24)

<400> SEQUENCE: 11
```

Asp Gly Xaa Xaa Thr Xaa Gly Xaa Ala Xaa Glu Ala Xaa Asn Xaa Ala
 1               5                  10                  15

Gly Xaa Xaa Xaa Leu Asn Asp Asn
            20

```
<210> SEQ ID NO 12
<211> LENGTH: 1400
<212> TYPE: DNA
<213> ORGANISM: Mentha piperita

<400> SEQUENCE: 12
gagttatcaa gagcagtttc ttgccatcgc tccattctga ggattctacc ttcttatcac     60
gtgctcctac ttctcttccc ctcaaaaatc ataagttaaa tgtggtagca gctctccaac    120
aagatagttc gaacgacgtc gttcctagcg gagacaggct gagccggccg aaatcaagag    180
cactgagttt caccggagag aagcctccca ttcctatact ggacaccatc aactacccta    240
atcacatgaa aaatctttcc gtcgaggaac tcgcaaacct agctgatgaa ctgagggaag    300
agatagtgta cacggtgtcg aaaaccggcg gccatcttag ctcgagccta ggcgtgtcgg    360
agctcaccgt cgcacttcat cacgttttca acacgcccga tgacaaaatc atctgggacg    420
tcggccacca ggcttaccca cacaaaatct tgaccgggag aagagcgaga atgcacacaa    480
```

-continued

| | | | | | |
|---|---|---|---|---|---|
| ttaggcagac | atttggatta | gcaggtttcc | ctaagagaga | tgaaagtgct | cacgatgcct | 540 |
| tcggcgccgg | ccatagttct | accagtattt | ctgctggttt | agggatggcg | gtggcgagag | 600 |
| atttactgca | gaagaacaac | cacgtcatat | cggtgatcgg | cgacggcgcc | atgacagctg | 660 |
| gacaagcgta | cgaggcctta | aacaacgccg | gattcctcga | ttcgaatctc | ataatcgttt | 720 |
| taaacgacaa | caagcaggtg | tctctaccca | cggccaccgt | cgacggccct | gcgccgccgg | 780 |
| tcggagctct | gagcaaagcc | ctgaccaagc | tgcaagccag | cagaaaattc | cggcagctcc | 840 |
| gcgaagcagc | aaagagtatg | actaagcaga | tgggagcacc | ggcacatgaa | atagcttcga | 900 |
| agttgacaca | atacgtgaaa | gggatgatgg | ggaaaccagg | cgcttcactt | ttcgaagaac | 960 |
| tggggattta | ttacatcgga | ccagtcgacg | gccataacgt | tgaagatctt | gtttatattt | 1020 |
| tcaagaaagt | taaggaaatg | cctgcgcctg | ggcctgttct | tattcatatc | atcaccgaaa | 1080 |
| aaggcaaagg | ctacccccct | gcagaaattg | ctgccgacaa | aatgcatggg | gtggtgaagt | 1140 |
| ttgatgcgaa | aactgggaaa | cagatgaaga | cgaagaacaa | gacgaagtca | tacacccagt | 1200 |
| acttcgccga | gtctctggtg | gcggaggcgg | agcacgacga | caagatcgtg | gcgatccacg | 1260 |
| ccgccatggg | gggcggcacc | gggctcaaca | tcttccagaa | gcagttcccg | gaccggtgct | 1320 |
| tcgacgtcgg | gatcgcggag | cagcacgcgg | tgacgttcgc | cgccggtatg | gcggcggagg | 1380 |
| ggctgaagcc | tttctgcgcc | | | | | 1400 |

NUCLEIC AND AMINO ACID SEQUENCES RELATING TO A NOVEL TRANSKETOLASE, AND METHODS FOR THE EXPRESSION THEREOF

This application claims the benefit of U.S. Provisional No. 60/056,033 filed Sep. 2, 1997.

This invention was funded, in part, by U.S. Department of Energy Grant No. DE-FG03-96ER20212. The United States government may have certain rights in the invention.

FIELD OF THE INVENTION

The present invention relates to nucleic acid sequences which code for a novel transketolase from peppermint (*Mentha x piperita*), and to vectors containing the sequences, host cells containing the sequences and methods of upregulating or downregulating the production or activity of the transketolases and their mutants.

BACKGROUND OF THE INVENTION

The isoprenoids comprise the largest family of natural products with over 20,000 individual compounds described to date (Connolly, J. D. & Hill, R. A., *Dictionary of Terpenoids* (Chapman and Hall, London, 1991)). The isoprenoids play numerous functional roles in plants as hormones (gibberelins, abscisic acid), photosynthetic pigments (side chain of phytol carotenoids), electron carriers (side chain of plastoquinone), and structural components of membranes (phytosterols). Isoprenoids also serve in communication and defense, for example as attractants for pollinators and seed dispersers, and as competitive phytotoxins, antibiotics, and herbivore repellents and toxins (Harborne, J. B. in *Ecological Chemistry and Biochemistry of Plant Terpenoids* (Harborne, J. B., Tomas-Berbean, F. A, Eds.), pp. 399–426 (Clarendon Press, Oxford, 1991)).

Until recently, it was generally assumed that all isoprenoids were synthesized from acetyl-CoA via the classical mevalonate pathway (Spurgeon, S. L. & Porter, J. W., Eds., in *Biosynthesis of Isoprenoid Compounds*, Vol. 1, pp 1–46 (John Wiley, New York, 1983)). However, in 1993, Rohmer and co-workers (Rohmer, M. et al., *Biochem. J.* 295:517–524 (1993)) demonstrated that a non-mevalonate pathway, originating from pyruvate and glyceraldehyde-3-phosphate (GAP) (Rohmer, M. et al., *J. Am. Chem. Soc.* 118:2564–2566 (1996)), operated in several eubacteria, including *E. coli*. Evidence subsequently emerged that the plastid-derived isoprenoids of plants, including carotenoids and the prenyl side chains of chlorophyll and plastoquinone (Lichtenthaler, H. K. et al., *FEBS Lett.* 400:271–274 (1997)), as well as isoprene (Zeidler J. G. et al., *Z. Naturforsch* 52c:15–23 (1997)), monoterpenes (Eisenreich, W. et al., *Tetrahedron Lett.* 38:3889–3892 (1997)) and diterpenes (Eisenreich, W. et al., *Proc. Natl. Acad. Sci. USA* 93:6431–6436 (1996)); (Schwarz, M. K., PhD thesis, ETH, Zurich, Switzerland (1994)), are synthesized via the pyruvate/GAP route to isopentenyl diphosphate (IPP). This new pathway had been completely overlooked in the past.

The first dedicated reaction of this new enzymatic pathway to IPP is considered to involve a transketolase-type condensation involving pyruvate and GAP to form 1-deoxy-D-xylulose-5-phosphate (Rohmer, M. et al., *J. Am. Chem. Soc.* 118:2564–2566 (1996)); (Zeidler J. G. et al., *Z. Naturforsch.* 52c:15–23 (1997)); (Broers, S. T. J., PhD thesis, ETH, Zurich, Switzerland (1994)) (FIG. 1). A recent abstract has described the cloning of a gene encoding 1-deoxyxylulose-5-phosphate synthase from *E. coli*, but no sequence information, or other descriptive information, was reported (Lois, L. M. et al., Third Terpnet Meeting of the European Network on Plant Isoprenoids, Poitiers, France, May 29–30 (1997)).

SUMMARY OF THE INVENTION

In accordance with the present invention, isolated nucleic acid sequences, such as the sequences set forth in SEQ ID NO: 1, SEQ ID NO:2, SEQ ID NO:3, SEQ ID NO:5 and SEQ ID NO:7 which encode all or part of a 1-deoxyxylulose-5-phosphate synthase (abbreviated as DXPS) from peppermint (*Mentha x piperita*) have been isolated, identified and characterized. Thus, the present invention provides nucleic acid sequences encoding plant 1-deoxyxylulose-5-phosphate synthase proteins. In particular, the present invention provides nucleic acid sequences encoding 1-deoxyxylulose-5-phosphate synthase proteins from the essential oil plants. In another aspect the present invention provides for isolated, recombinant DXPS proteins, such as the proteins having the sequences set forth in SEQ ID NO:4, SEQ ID NO:6 and SEQ ID NO:8. In other aspects, the present invention is directed to replicable recombinant cloning vehicles comprising a nucleic acid sequence, e.g., a DNA sequence, which codes for DXPS or for a base sequence sufficiently complementary to at least a portion of the DXPS DNA or RNA to enable hybridization therewith (e.g., antisense transketolase RNA or fragments of complementary transketolase DNA which are useful as polymerase chain reaction primers or as probes for transketolases from *Mentha x piperita* or related genes). In yet other aspects of the invention, modified host cells are provided that have been transformed, transfected, infected and/or injected with a recombinant cloning vehicle and/or DNA sequence of the invention. Thus, the present invention provides for the recombinant expression of the transketolase 1-deoxyxylulose-5-phosphate synthase (DXPS) from peppermint (*Mentha x piperita*) and related transketolases, and the inventive concepts may be used to facilitate the production, isolation and purification of significant quantities of recombinant transketolases (or of the primary enzyme products) for subsequent use, such as to obtain expression or enhanced expression of transketolases in plants to attain enhanced production of predator or pathogen defense compounds, or may be otherwise employed in an environment where the regulation or expression of transketolases are desired. In other aspects, the regulation of isoprenoid biosynthesis in plants by transforming, transfecting, infecting and/or injecting the plant with a recombinant cloning vehicle and/or DNA sequence of the invention to obtain expression of the transketolase DXPS or a related transketolse in the plant and thereby upregulate the pyruvate/glyceraldehyde-3-phosphate isoprenoid biosynthetic pathway. Thus, in addition to the new nucleic acid sequences and fragments thereof, the present invention includes new vectors containing the sequences, host cells containing the sequences, isolated recombinant transketolase (synthase) polypeptides and methods of producing recombinant transketolases ad their mutants.

BRIEF DESCRIPTION OF THE DRAWINGS

The foregoing aspects and many of the attendant advantages of this invention will be better understood by reference to the following detailed description, when taken in conjunction with the accompanying drawings, wherein.

DETAILED DESCRIPTION OF THE PREFERRED EMBODIMENT

Figure 1:
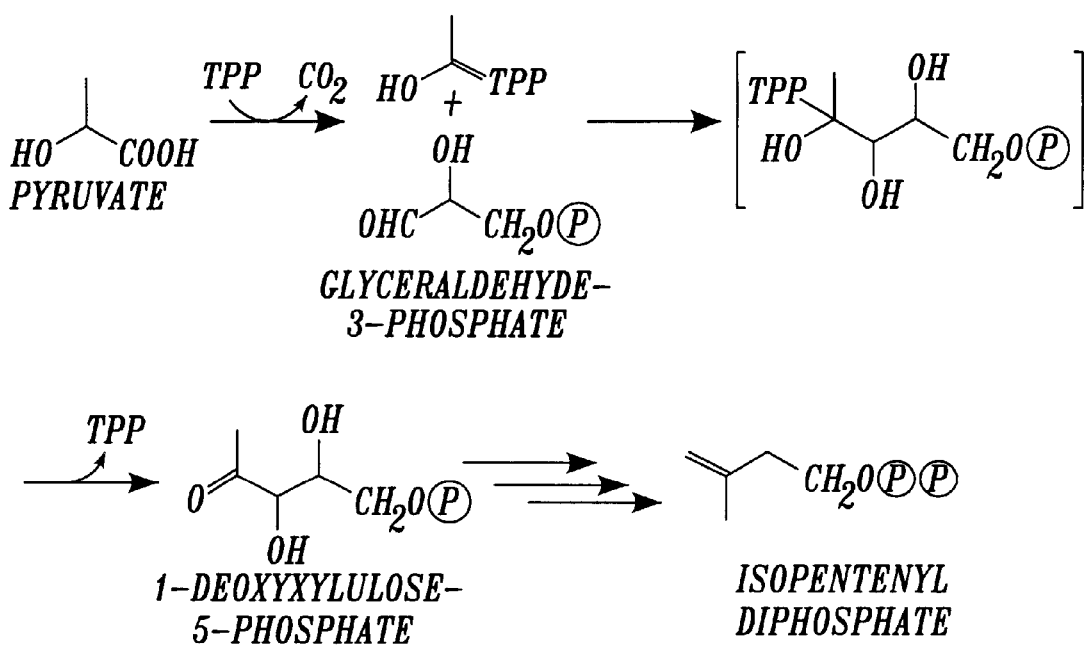
FIG. 1 is a schematic representation of the enzymatic pathway from pyruvate to isopentenyl diphosphate IPP) as catalyzed by 1-deoxyxylulose-5-phosphate synthase (DXPS). The addition of thiamin pyrophosphate (TPP)-activated acetaldehyde, formed by decarboxylation of pyruvate, to C1 of glyceraldehyde- 3-phosphate (GAP) and subsequent loss of TPP yields 1-deoxyxylulose-5-phosphate, which ultimately gives rise to isopentenyl diphosphate (IPP).

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "1-deoxyxylulose-5-phosphate synthase" (abbreviated as "DXPS") is used herein to mean an enzyme capable of catalyzing a transketolase-type condensation involving pyruvate and glyceraldehyde-3-phosphate (GAP) to form 1-deoxy-D-xylulose-5-phosphate. This reaction is schematically set forth in FIG. 1.

The term "essential oil plant," or "essential oil plants," refers to a group of plant species that produce high levels of monoterpenoid and/or sesquiterpenoid and/or diterpenoid oils, and/or high levels of monoterpenoid and/or sesquiterpenoid and/or diterpenoid resins. The foregoing oils and/or resins account for greater than about 0.005% of the fresh weight of an essential oil plant that produces them. The essential oils and/or resins are more fully described, for example, in E. Guenther, *The Essential Oils*, Vols. I–VI, R. E. Krieger Publishing Co., Huntington, N.Y., 1975, incorporated herein by reference. The essential oil plants include, but are not limited to:

Lamiaceae, including, but not limited to, the following species: Ocimum (basil), Lavandula (Lavender), Origanum (oregano), Mentha (mint), Salvia (sage), Rosmecinus (rosemary), Thymus (thyme), Satureja and Monarda.

Umbelliferae, including, but not limited to, the following species: Carum (caraway), Anethum (dill), feniculum (fennel) and Daucus (carrot).

Asteraceae (Compositae), including, but not limited to, the following species: Artemisia (tarragon, sage brush), Tanacetum (tansy).

Rutaceae (e.g., citrus plants); Rosaceae (e.g., roses); Myrtaceae (e.g., eucalyptus, Melaleuca); the Gramineae (e.g., Cymbopogon (citronella)); Geranaceae (Geranium) and certain conifers including Abies (e.g., Canadian balsam), Cedrus (cedar) and Thuja and Juniperus.

The range of essential oil plants is more fully set forth in E. Guenther, *The Essential Oils*, Vols. I–VI, R. E. Krieger Publishing Co., Huntington, N.Y., 1975, which is incorporated herein by reference.

Abbreviations used are: bp, base pair; DMAPP, dimethylallyl diphosphate; DXPS, 1-deoxyxylulose-5-phosphate synthase; GAP, glyceraldehyde-3-phosphate; IPP, isopentenyl diphosphate;; Mopso, 3 -(N-morpholino)-2-hydroxypropane-sulfonic acid; Tris, Tris-(hydroxymethyl) aminomethane; UTR, untranslated region; TLC, thin layer chromatography; Tr, truncation site; GC, gas chromatography; Hepes, N-2-hydroxyethylpiperazine-N'-2-ethanesulfonic acid; kb, kilobase pairs.

The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

The terms "alteration", "amino acid sequence alteration", "variant" and "amino acid sequence variant" refer to 1-deoxyxylulose5-phosphate synthase molecules with some differences in their amino acid sequences as compared to the corresponding, native, i.e., naturally-occurring, 1-deoxyxylulose-5-phosphate syntheses. Ordinarily, the variants will possess at least about 70% homology with the corresponding native 1-deoxyxylulose-5-phosphate synthases, and preferably they will be at least about 80% homologous with the corresponding, native 1-deoxyxylulose-5-phosphate synthases. The amino acid sequence variants of the 1-deoxyxylulose-5-phosphate synthases falling within this invention possess substitutions, deletions, and/or insertions at certain positions. Sequence variants of 1-deoxyxylulose-5-phosphate synthases may be used to attain desired enhanced or reduced enzymatic activity, modified regiochemistry or stereochemistry, or altered substrate utilization or product distribution.

Substitutional 1-deoxyxylulose-5-phosphate synthase variants are those that have at least one amino acid residue in the native 1-deoxyxylulose-5-phosphate synthase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the 1-deoxyxylulose-5-phosphate synthase molecules of the present invention may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the 1-deoxyxylulose-5-phosphate synthase molecules of the present invention would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional 1-deoxyxylulose-5-phosphate synthase variants are those with one or more amino acids inserted immediately adjacent to an amino acid at a particular position in the native 1-deoxyxylulose-5-phosphate synthase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native 1-deoxyxylulose-5-phosphate synthase molecules have been removed. Ordinarily, deletional variants will have one or two amino acids deleted in a particular region of the 1-deoxyxylulose-5-phosphate synthase molecule.

The terms "biological activity", "biologically active", "activity" and "active" refer to the ability of the 1-deoxyxylulose-5-phosphate synthases of the present invention to catalyze a transketolase-type condensation involving pyruvate and glyceraldehyde-3-phosphate (GAP) to form 1-deoxy-D-xylulose-5-phosphate. This reaction is schematically set forth in FIG. 1. 1-deoxyxylulose-5-phosphate synthase activity is measured in an enzyme activity assay, such as the assay described in Example 2. Amino acid sequence variants of the 1-deoxyxylulose-5-phosphate synthases of the present invention may have desirable altered biological activity including, for example, altered reaction kinetics, substrate utilization, product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of DNA (the insert DNA) from another source. The vector is used to transport the insert DNA into a suitable host cell. The insert DNA may be derived from the host cell, or may be derived from a different cell or organism. Once in the host cell, the vector can replicate independently of or coincidental with the host chromosomal DNA, and several copies of the vector and its inserted DNA may be generated. In addition, the vector contains the necessary elements that permit translating the insert DNA into a polypeptide. Many molecules of the polypeptide encoded by the inset DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, total RNA was extracted from secretory cells which had been isolated from 5-day-old peppermint leaves. Poly(A)$^+$-RNA was purified by chromatography on oligo(dT)-cellulose (Pharmacia), and 5 μg of the resulting mRNA was utilized to construct a λZAP cDNA library. One hundred and fifty randomly picked and purified clones were in vivo-excised and the resulting phagemids were sequenced using T3 and T7 primers. Two clones (designated pDS1 and pDS2) were identified which exhibited significant sequence similarity to a recently described *Arabidopsis thaliana* transketolase gene of unknown function (CLA1). The nucleotide sequence of the cDNA insert of pDS1 is set forth in SEQ ID NO:1, and the nucleotide sequence of the cDNA insert of pDS2 is set forth in SEQ ID NO:2.

A set of 3,000 plaques was then screened with a nucleic acid probe (SEQ ID NO:9) derived by PCR from the cDNA insert (SEQ ID NO:1) of pDS1. This procedure afforded 47 positive signals under high-stringency hybridization conditions. After one additional cycle of hybridization, the positive clones were in vivo-excised, the insert sizes were determined by PCR, and the 20 largest clones were partially sequenced. Three of these clones (designated pDS16, pDS29 and pDS39) appeared to be of full-length and were entirely sequenced on both strands. The nucleotide sequence of the cDNA insert of pDS16 is set forth in SEQ ID NO:3, the nucleotide sequence of the cDNA insert of pDS29 is set forth in SEQ ID NO:5 and the nucleotide sequence of the cDNA insert of pDS39 is set forth in SEQ ID NO:7.

The cDNA insert of DXPS clone pDS29 (SEQ ID NO:5), which yielded the highest expressed level of synthase activity, contains an open reading frame (ORF) of 2172 nucleotides. The first 70 deduced amino acid residues (amino acid residues 1–70 of SEQ ID NO:6) show the general characteristics of plastidial targeting sequences, consistent with the proposed subcellular location of the enzyme in plant cells. By excluding the putative transit peptide residues, the sequence corresponds to a mature protein of about 650 amino acids, with a predicted size of roughly 71 kDa. An alignment of translated transketolase sequences (devoid of plastid-targeting peptides where appropriate) shows very high similarity/identity values between the peppermint DXPS and several other transketolases.

Figure 2A:
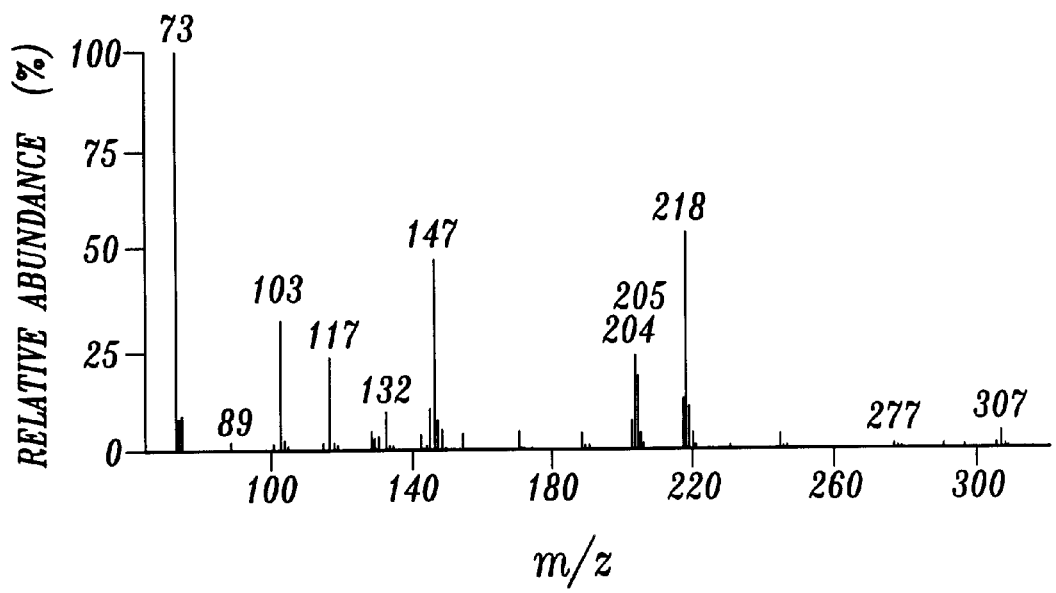
FIG. 2A shows a GC-MS analysis of the product formed by the recombinant DXPS peppermint enzyme. Mass fragmentation patterns are illustrated for the biosynthetic product after dephosphorylation and trimethylsilylation ($R_t$=6.71 min).
Figure 2B:
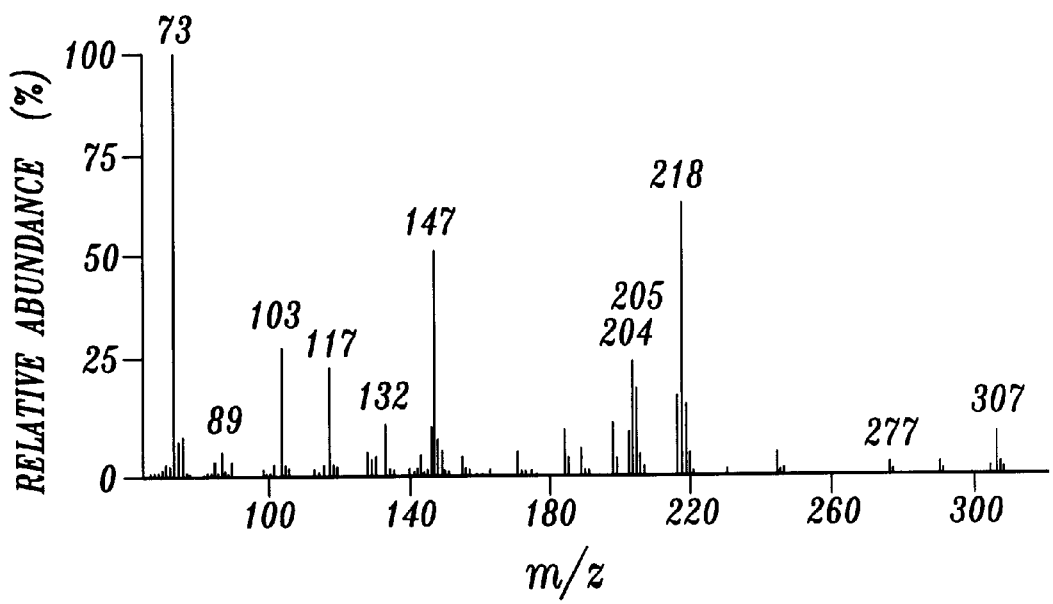
FIG. 2B shows a GC-MS analysis of the silylated derivative of authentic 1-deoxy-D-xylulose ($R_f$=6.70 min).

E. coli cultures transfected with phagemids derived from pDS16, including the cDNA sequence set forth in SEQ ID NO:3, pDS29, including the cDNA sequence set forth in SEQ ID NO:5, and pDS39, including the cDNA sequence set forth in SEQ ID NO:7, were each induced with isopropyl-1 thio-β D-galactopyranoside (IPTG), the corresponding bacterial cells were harvested and homogenized, and the extracts were assayed using [2-$^{14}$C] pyruvate and D,L-glyceraldehyde-3 phosphate as co-substrates. Preparations from E. coli cells transfected with pDS29, including the cDNA sequence set forth in SEQ ID NO:5, and pDS39, including the cDNA sequence set forth in SEQ ID NO:7, yielded a prominent new radioactive component in the reaction mixture that, upon reversed-phase ion-pair radio-HPLC, exhibited a $R_t$ (35.5 min) consistent with that of a sugar (pentulose) phosphate. The same enzymatic product was generated with D-glyceraldehyde-3 -phosphate as co-substrate, indicating that the D-antipode is the likely natural substrate of the functionally expressed transketolase. The presumptive pentulose phosphate product from preparative enzyme incubations (E. coli transformed with pDS29, including the cDNA sequence set forth in SEQ ID NO:5) was purified by HPLC and hydrolyzed with acid phosphatase, and the resulting sugar was silylated. This derivatized product of the recombinant enzyme was then analyzed by combined capillary GC-MS and shown to possess the identical retention time (6.71±0.03 min) and mass spectrum as that of an authentic sample of silylated 1-deoxy-D-xylulose (FIGS. 2A and 2B). The combined evidence thus indicated that a cDNA encoding 1-deoxyxylulose-5-phosphate synthase (DXPS) had been acquired. DXPS activity was significantly higher in the IPTG-induced E. coli cells expressing the cDNA insert of pDS29 (SEQ ID NO:5), when compared to identically treated cells containing the same plasmid devoid of the cDNA insert set forth in SEQ ID NO:5 (7-fold higher than endogenous activity, n=7, p<0.01).

Figure 3:
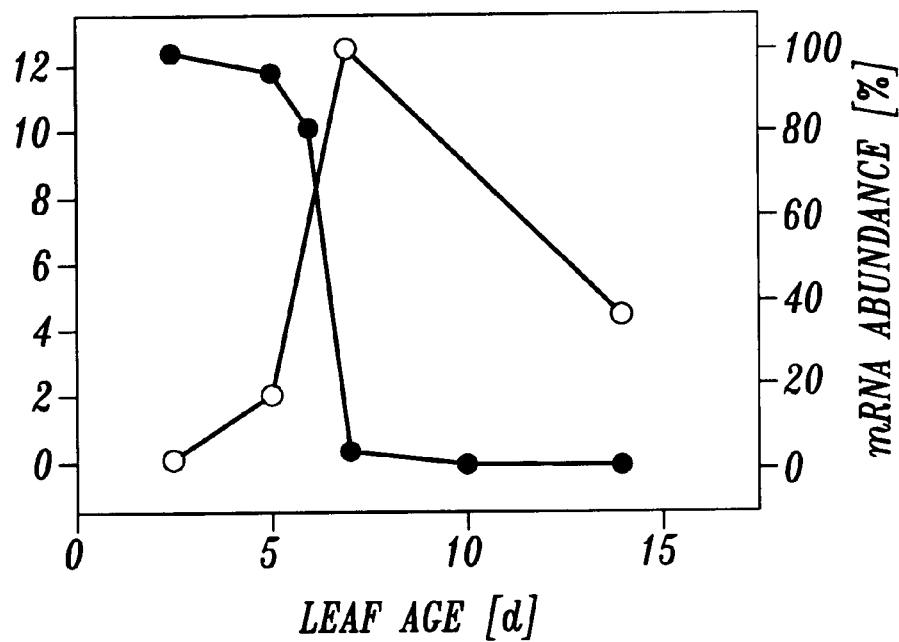
FIG. 3 is a graphical representation of the time-course of relative steady-state DXPS mRNA levels (—●—) and rate of monoterpene biosynthesis as measured by $^{14}CO_2$ incorporation (—○—) during leaf development in peppermint. Total RNA was isolated from oil gland secretory cells of leaves of different developmental stages. A $^{32}$P-labeled probe derived from DXPS clone pDS29 (SEQ ID NO:5) detected a transcript of about 3 kb. Leaves are fully expanded by two weeks, and high rates of monoterpene biosynthesis and high steady-state levels of DXPS mRNA are observed only during early leaf development (<7 d).

RNA blot analyses showed a direct correlation between steady-state levels of the DXPS message and monoterpene production, as determined by $CO_2$ incorporation, thus suggesting activation of the non-mevalonate pathway to supply the IPP precursor for subsequent monoterpene biosynthesis in peppermint oil glands (FIG. 3).

The isolation of fill-length cDNAs (SEQ ID NO:3, SEQ ID NO:5, SEQ ID NO:7) encoding 1-deoxyxylulose-5-phosphate synthase permits the development of efficient expression systems for this functional enzyme; provides useful tools for examining the developmental regulation of DXPS; permits investigation of the reaction mechanism(s) of this enzyme, and permits the isolation of other 1-deoxyxylulose-5-phosphate synthases. The isolation of full-length 1-deoxyxylulose-5-phosphate synthase cDNAs (SEQ ID NO:3, SEQ ID NO:5, SEQ ID NO:7) also permits the transformation of a wide range of organisms in order to enhance, or otherwise alter, the synthesis of 1-deoxyxylulose-5-phosphate, and of its derivatives, such as IPP.

Although the full-length 1-deoxyxylulose-5-phosphate synthase proteins set forth in (SEQ ID NO:4, SEQ ID NO:6, SEQ ID NO:8) directs the enzyme to plastids, substitution of the presumptive targeting sequence of this enzyme (e.g., SEQ ID NO:3, amino acid residue numbers 1 to 70) with other transport sequences well known in the art (see, e.g., von Heijne et al., *Eur. J. Biochem.*, 180:535–545, 1989; Stryer, *Biochemistry*, W. H. Freeman and Company, New York, N.Y., p. 769 [1988]) may be employed to direct 1-deoxyxylulose-5-phosphate synthase to other cellular or extracellular locations.

In addition to the native 1-deoxyxylulose-5-phosphate synthase amino acid sequences of SEQ ID NO:4, SEQ ID NO:6, SEQ ID NO:8, sequence variants produced by deletions, substitutions, mutations and/or insertions are intended to be within the scope of the invention except insofar as limited by the prior art. The 1-deoxyxylulose-5-phosphate synthase amino acid sequence variants of this invention may be constructed by mutating the DNA sequences that encode the wild-type synthases, such as by using techniques commonly referred to as site-directed mutagenesis. Nucleic acid molecules encoding the 1-deoxyxylulose-5-phosphate synthases of the present invention can be mutated by a variety of PCR techniques well known to one of ordinary skill in the art. (See, for example, the following publications, the cited portions of which are incorporated by reference herein: "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, NY (1990).

By way of non-limiting example, the two primer system utilize in the Transformer Site-Directed Mutagenesis kit from Clontech, may be employed for introducing site-directed mutants into the 1-deoxyxylulose-5-phosphate synthase genes of the present invention. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be fully sequenced or restricted and analyzed by electrophoresis on Mutation Detection Enhancement gel (J. T. Baker) to confirm that no other alterations in the sequence have occurred (by band shift comparison to the unmutagenized control).

Again, by way of non-limiting example, the two primer system utilized in the QuikChange™ Site-Directed Mutagenesis kit from Stratagene (LaJolla, Calif.), may be employed for introducing site-directed mutants into the 1-deoxyxylulose-5-phosphate synthase genes of the present invention. Double-stranded plasmid DNA, containing the insert bearing the target mutation site, is denatured and mixed with two oligonucleotides complementary to each of the strands of the plasmid DNA at the target mutation site. The annealed oligonucleotide primers are extended using Pfu DNA polymerase, thereby generating a mutated plasmid containing staggered nicks. After temperature cycling, the unmutated, parental DNA template is digested with restriction enzyme DpnI which cleaves methylated or hemimethylated DNA, but which does not cleave unmethylated DNA. The parental, template DNA is almost always methylated or hemimethylated since most strains of *E. coli*, from which the template DNA is obtained, contain the required methylase activity. The remaining, annealed vector DNA incorporating the desired mutation(s) is transformed into *E. coli*.

The sequence verified mutant duplexes in the pET (or other) overexpression vector can be employed to transform *E. coli* such as strain *E. coli* BL21(D)E3)pLysS, for high level production of the mutant protein, and purification by standard protocols. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutagenesis, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His.

Other site directed mutagenesis techniques may also be employed with the nucleotide sequences of the invention. For example, restriction endonuclease digestion of DNA followed by ligation may be used to generate deletion variants of 1-deoxyxylulose-5-phosphate synthase, as described in section 15.3 of Sambrook et al. *Molecular Cloning: A Laboratory Manual*, 2nd Ed., Cold Spring Harbor Laboratory Press, New York, N.Y. [1989], incorporated herein by reference. A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 [1983]); Sambrook et al., supra; "Current Protocols in Molecular Biology", 1991, Wiley (NY), F. T. Ausubel, R. Brent, R. E. Kingston, D. D. Moore, J. D. Seidman, J. A. Smith and K. Struhl, eds, incorporated herein by reference.

Generally, oligonucleotides of at least 25 nucleotides in length are used to insert, delete or substitute two or more nucleotides in the 1-deoxyxylulose-5-phosphate synthase molecule. An optimal oligonucleotide will have 12 to 15 perfectly matched nucleotides on either side of the nucleotides coding for the mutation. To mutagenize wild-type 1-deoxyxylulose-5-phosphate synthase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type synthase inserted in the vector, and the second strand of DNA encodes the mutated form of the synthase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type 1-deoxyxylulose-5-phosphate synthase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

A gene encoding 1-deoxyxylulose-5-phosphate synthase may be incorporated into any organism (intact plant, animal, microbe, etc.), or cell culture derived therefrom. A 1-deoxyxylulose-5-phosphate synthase gene may be introduced into any organism for a variety of purposes including, but not limited to: production of 1-deoxyxylulose-5-phosphate synthase, or its product 1-deoxyxylulose-5-phosphate; enhancement of the rate of production and/or the absolute amount of one or more chemical compounds, such as IPP, derived from 1-deoxyxylulose-5-phosphate; augmenting the disease resistance of plants by enhancing the production of terpenoid(s) having defensive, e.g., antimicrobial or antifeedant, properties. Additionally, a gene encoding all or part of a 1-deoxyxylulose-5-phosphate synthase can be introduced, in antisense orientation, into any plant species in order to reduce the amount of 1-deoxyxylulose-5-phosphate synthase produced in the plant, thereby reducing the production of terpenoids.

Additionally, because the novel pathway involving the DXPS enzymes of the present invention is present in certain bacteria and plants, but not in animals, it provides a new molecular target for the design of highly specific antibiotics and herbicides. Thus, analysis of the structure and catalytic mechanism of DXPS proteins of the present invention will lead to the development of selective inhibitors of this enzyme having antibiotic and/or herbicidal activity. Once selective inhibitors of the DXPS proteins of the present invention have been identified, mutagenesis of the nucleic acid molecules encoding DXPS proteins of the present invention will yield inhibitor-resistant DXPS proteins. Nucleic acid sequences encoding these inhibitor-resistant DXPS proteins can be introduced into plants, thereby producing transgenic plants that are resistant to the DXPS inhibitors. Thus, for example, transgenic grass species used in lawns can be transformed with a nucleic acid sequence encoding inhibitor-resistant DXPS protein; thereafter treatment of the lawn with a DXPS inhibitor will kill unwanted weeds, but leave the transformed, DXPS-resistant grass unharmed.

Eukaryotic expression systems may be utilized for the production of 1-deoxyxylulose-5-phosphate synthase since they are capable of carrying out any required posttranslational modifications and of directing the enzyme to the proper cellular compartment. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Bio-technology,* 6:47–55 [1987]) for expression of the 1-deoxyxylulose-5-phosphate synthases of the invention. Infection of insect cells (such as cells of the species *Spodoptera frugiperda*) with the recombinant baculoviruses allows for the production of large amounts of the 1-deoxyxylulose-5-phosphate synthase proteins. In addition, the baculovirus system has other important advantages for the production of recombinant 1-deoxyxylulose-5-phosphate synthase. For example, baculoviruses do not infect humans and can therefore be safely handled in large quantities. In the baculovirus system, a DNA construct is prepared including a DNA segment encoding 1-deoxyxylulose-5-phosphate synthase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/1-deoxyxylulose-5-phosphate synthase combination is flanked on both sides by 200–300 base pairs of baculovirus DNA (the flanking sequences).

To produce the 1-deoxyxylulose-5-phosphate synthase DNA construct, a cDNA clone encoding the full length 1-deoxyxylulose-5-phosphate synthase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full 1-deoxyxylulose-5-phosphate synthase. For example, an insect host cell can be cotransfected or transfected separately with the DNA construct and a functional baculovirus. Resulting recombinant baculoviruses can then be isolated and used to infect cells to effect production of the 1-deoxyxylulose-5-phosphate synthase. Host insect cells include, for example, *Spodoptera frugiperda* cells, that are capable of producing a baculovirus-expressed 1-deoxyxylulose-5-phosphate synthase. Insect host cells infected with a recombinant baculovirus of the present invention are then cultured under conditions allowing expression of the baculovirus-encoded 1-deoxyxylulose-5-phosphate synthase. 1-deoxyxyluose-5-phosphate synthase thus produced is then extracted from the cells using methods known in the art.

Other eukaryotic microbes such as yeasts may also be used to practice this invention. The baker's yeast *Saccharomyces cerevisiae,* is a commonly used yeast, although several other strains are available. The plasmid YRp7 (Stinchcomb et al., *Nature,* 282:39 [1979]; Kingsman et al., *Gene* 7:141 [1979]; Tschemper et al., *Gene,* 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics,* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA,* 75:1929 [1978]). Additional yeast transformation protocols are set forth in Gietz et al., *N.A.R,* 20(17):1425(1992); Reeves et al., *FEMS,* 99(2–3):193–197, (1992), both of which references are incorporated herein by reference.

Suitable promoting sequences in yeast vectors include the promoters for 3-phosphoglycerate kinase (Hitzeman et al.,*J. Biol. Chem.,* 255:2073 [1980]) or other glycolytic enzymes (Hess et al., *J. Adv. Enzyme Reg.* 7:149 [1968]; Holland et al., *Biochemistry,* 17:4900 [1978]), such as enolase, glyceraldehyde-3-phosphate dehydrogenase, hexokinase, pyruvate decarboxylase, phosphofructokinase, glucose-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode 1-deoxyxylulose-5-phosphate synthase and a selectable marker gene, e.g., the kan gene encoding resistance to kanamycin, into *Agrobacterium tumifaciens* containing a helper Ti plasmid as described in Hoeckema et al., *Nature,* 303:179–181 [1983] and culturing the Agrobacterium cells with leaf slices, or other tissues or cells, of the plant to be transformed as described by An et al., *Plant Physiology,* 81:301–305 [1986]. Transformation of cultured plant host cells is normally accomplished through *Agrobacterium tumifaciens*. Cultures of mammalian host cells and other host cells that do not have rigid cell membrane barriers are usually transformed using the calcium phosphate method as originally described by Graham and Van der Eb (*Virology,* 52:546 [1978]) and modified as described in sections 16.32–16.37 of Sambrook et al., supra. However, other methods for introducing DNA into cells such as Polybrene (Kawai and Nishizawa, *Mol. Cell. Biol.,* 4:1172 [1984]), protoplast fusion (Schaffner, *Proc. Natl. Acad. Sci. USA,* 77:2163 [1980]), electroporation (Neumann et al., *EMBO J.,* 1:841 [1982]), and direct microinjection into nuclei (Capecchi, *Cell,* 22:479 [1980]) may also be used. Additionally, animal transformation strategies are reviewed in Monastersky G. M. and Robl, J. M., *Strategies in Transgenic Animal Science,* ASM Press, Washington, D.C., 1995. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated an and the resulting plants transferred to soil using techniques well known to those skilled in the art.

In addition, a gene regulating 1-deoxyxylulose-5-phosphate synthase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology,* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a 1-deoxyxylulose-5-phosphate synthase gene that previously has had its native promoter removed. This engineered gene is the combination of a promoter that responds to an external chemical stimulus and a gene responsible for successful production of 1-deoxyxylulose-5-phosphate synthase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology,* CRC Press, Boca Raton, Fla. [1993], incorporated by reference herein). Representative examples include electroporation-facilitated DNA uptake by protoplasts in which an electrical pulse transiently permeabilizes cell membranes, permitting the uptake of a variety of biological molecules, including recombinant DNA (Rhodes et al., *Science,* 240(4849) :204–207 [1988]); treatment of protoplasts with polyethylene glycol (Lyznik et al, *Plant Molecular Biology,* 13:151–161 [1989]); and bombardment of cells with DNA-laden microprojectiles which are propelled by explosive force or compressed gas to penetrate the cell wall (Klein et al., *Plant Physiol.* 91:440–444 [1989] and Boynton et al., *Science,* 240(4858):1534–1538 [1988]). Transformation of Taxus species can be achieved, for example, by employing the methods set forth in Han et al, *Plant Science,* 95:187–196 (1994), incorporated by reference herein. A method that has been applied to Rye plants (*Secale cereale*) is to directly inject plasmid DNA, including a selectable marker gene, into developing floral tillers (de la Pena et al., *Nature* 32S:274–276 (1987)). Further, plant viruses can be used as vectors to transfer genes to plant cells. Examples of plant viruses that can be used as vectors to transform plants include the Cauliflower Mosaic Virus (Brisson et al., *Nature* 310: 511–514 (1984); Additionally, plant transformation strategies and techniques are reviewed in Birch, R. G., *Ann Rev Plant Phys Plant Mol Biol,* 48:297 (1997); Forester et al., *Exp. Agric.,* 33:15–33 (1997). The aforementioned publications disclosing plant transformation techniques are incorporated herein by reference, and minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.,* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.,* 23:243 [1980]); monkey kidney cells (CVI-76, ATCC CCL 70); African green monkey kidney cells (VERO-76, ATCC CRL-1587); human cervical carcinoma cells (HELA ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells ARC, MI.54, Baumann et al., *J. Cell Bol.,* 85:1 [1980]); and TRI cells (Mather et al., *Annals N.Y. Acad Sci.,* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature,* 273:113 [1978]). Smaller or larger SV40 DNA fragments may also be used, provided they contain the approximately 250-bp sequence extending from the Hindi site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of 1-deoxyxylulose-5-phosphate synthase in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325) *E. coli* X1776 (ATCC No. 31,537), and *E. coli* B; however many other strains of *E. coli,* such as HB101, JM101, NM522, NM538, NM539, and many other species and genera of prokaryotes including bacilli such as *Bacillus subtilis,* other enterobacteriaceae such as *Salmonella typhimurium* or *Serratia marcesans,* and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enzymol.,* 204:63 (1991).

As a representative example, cDNA sequences encoding 1-deoxyxylulose-5-phosphate synthase may be transferred to the (His)$_6$.Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the 1-deoxyxylulose-5-phosphate synthase again purified by immobilized metal ion affinity chromatography, this time using a shallower imidazole gradient to elute the recombinant synthases while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature*, 375:615 [1978]; Itakura et al., *Science*, 198:1056 [1977]; Goeddel et al., *Nature*, 281:544 [1979]) and a tryptophan (trp) promoter system (Goeddel et al., *Nucl. Acids Res.*, 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell*, 20:269 [1980]).

Many eukaryotic proteins normally secreted from the cell contain an endogenous secretion signal sequence as part of the amino acid sequence. Thus, proteins normally found in the cytoplasm can be targeted for secretion by liking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W. H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.*, 11:1657 [1983]), α-factor, alkaline phosphatase and invertase may be used to direct secretion from yeast host cells. Prokaryotic signal sequences from genes encoding, for example, LamB or OmpF (Wong et al., *Gene*, 68:193 [1988]), MalE, PhoA, or beta-lactamase, as well as other genes, may be used to target proteins from prokaryotic cells into the culture medium.

Trafficking sequences from plants, animals and microbes can be employed in the practice of the invention to direct the 1-deoxyxylulose-5-phosphate synthase proteins of the present invention to the cytoplasm, endoplasmic reticulum, mitochondria or other cellular components, or to target the protein for export to the medium. These considerations apply to the overexpression of 1-deoxyxylulose-5-phosphate synthase, and to direction of expression within cells or intact organisms to permit gene product function in any desired location.

The construction of suitable vectors containing DNA encoding replication sequences, regulatory sequences, phenotypic selection genes and the 1-deoxyxylulose-5-phosphate synthase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, 1-deoxyxylulose-5-phosphate synthase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA This procedure is known generally. For example, see Lawn et al. (*Nucleic Acids Res.*, 9:6103–6114 [1982]), and Goeddel et al. (*Nucleic Acids Res.*, supra).

These and other aspects of the present invention may be made more apparent in connection with the following representative examples that are presented for purposes of illustrating some of the inventive concepts.

EXAMPLE 1 cDNA Library Construction and Screening cDNA Library Construction and Screening. Peppermint (*Mentha x piperita*) leaf secretory cells are highly specialized for isoprenoid (monoterpene essential oil) formation and, thus, a highly enriched source of mRNA species encoding proteins involved in essential oil biosynthesis. Consequently, total RNA was extracted (Logemann, J. et al., *Anal. Biochem.* 163:16–20 (1987)) from secretory cells which had been isolated from 5day-old peppermint leaves (Gershenzon, J. et al., *Anal. Biochem.* 200:130–138 (1992)).

Poly(A)⁺-RNA was purified by chromatography on oligo (dT)-cellulose (Pharmacia), and 5 μg of the resulting mRNA was utilized to construct a λZAP cDNA library according to the manufacturers instructions (Stratagene). One hundred and fifty randomly picked and purified clones were in vivo-excised and the resulting phagemids were sequenced using T3 and T7 primers. In addition to several genes of known function in isoprenoid biosynthesis, two clones (designated pDS1 and pDS2) were identified which exhibited significant sequence similarity to a recently described *Arabidopsis thaliana* transketolase gene (CLA1) of unknown function, the disruption of which results in an albino mutant arrested in chloroplast development (Mandel, M. A. et al., *Plant J.* 9:649–658 (1996)). The nucleotide sequence of the cDNA insert of pDS1 is set forth in SEQ ID NO:1, and the nucleotide sequence of the cDNA insert of pDS2 is set forth in SEQ ID NO:2.

A set of 3,000 plaques was then screened with a nucleic acid probe (SEQ ID NO:9) derived by PCR from the pDS1 cDNA insert (SEQ ID NO: 1). This procedure afforded 47 positive signals under high-stringency hybridization conditions. After one additional cycle of hybridization, the positive clones were in vivo-excised, the insert sizes were determined by PCR, and the 20 largest clones were partially sequenced. Three of these clones (designated pDS16, pDS29 and pDS39) appeared to be full-length and were entirely sequenced on both strands. The nucleotide sequence of the cDNA insert of pDS16 is set forth in SEQ ID NO:3, the nucleotide sequence of the cDNA insert of pDS29 is set forth in SEQ ID NO:5 and the nucleotide sequence of the cDNA insert of pDS39 is set forth in SEQ ID NO:7.

Figure 4:
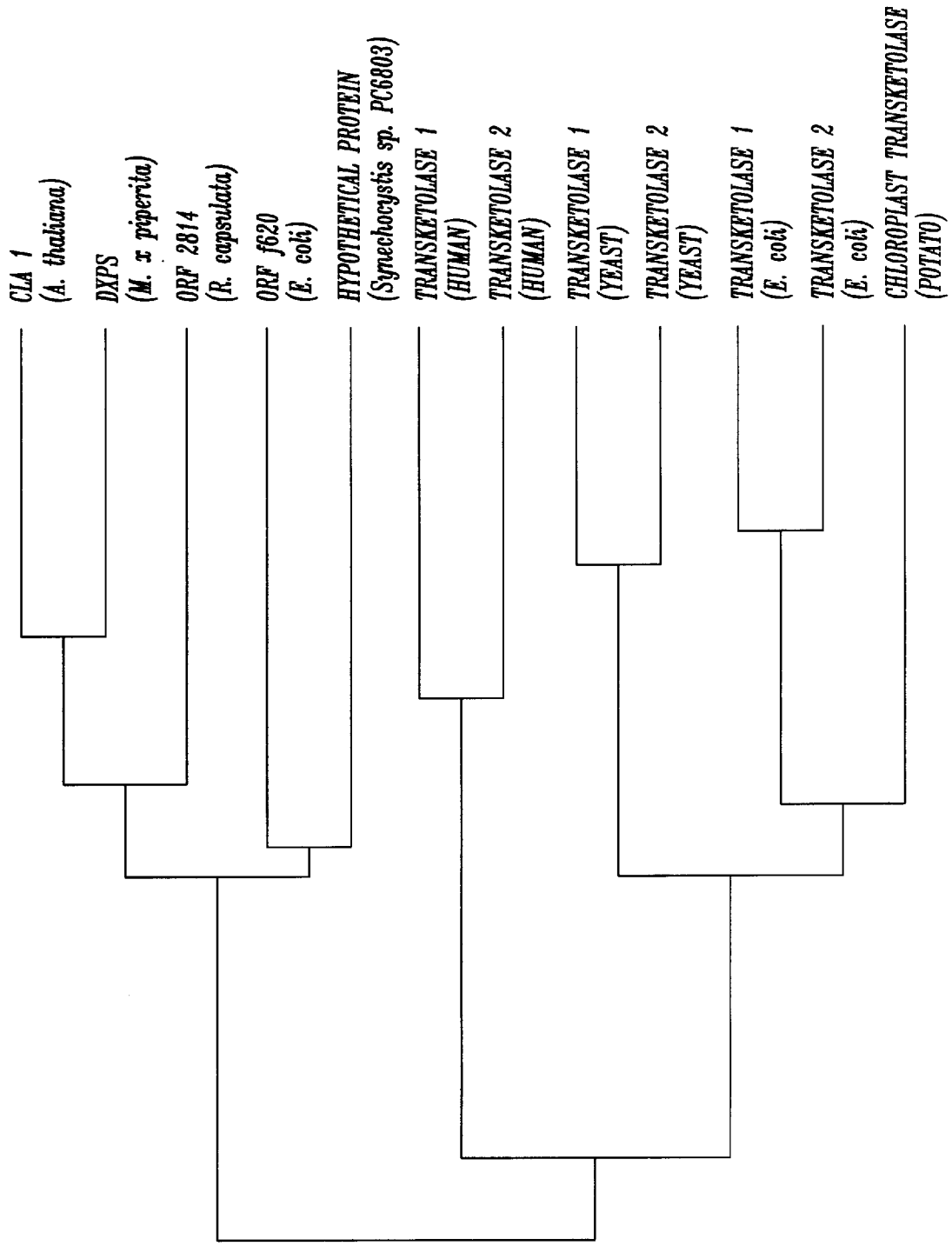
FIG. 4 shows the results of clustering relationship analysis based on sequence comparisons carried out using GCG version 9.0 of the University of Wisconsin Genetics Computer Group Package (1997). The following transketolase sequences are included: DXPS (*Mentha x piperita*, accession number AF019383), CLA1 (*Arabidopsis thaliana*, U27099), ORF2814 (*Rhodobacter capsulata*, P6242), ORFf620 (*Escherichia coli*, U82664), a protein of unknown function (Synechocystis sp. PC6803, D90903), transketolase 1 (human, A45050; yeast P23254; *Escherichia coli*, P27302), transketolase 2 (human, P51854; yeast, P33315; *Escherichia coli*, P33570), and a plastidial transketolase from potato (Z50099).

Structure of cDNA Insert of DXPS Clone pDS29 (SEQ ID NO:5). The cDNA insert of DXPS clone pDS29 (SEQ ID NO:5), which yielded the highest expressed level of synthase activity, contains an open reading frame (ORF) of 2172 nucleotides. The first 70 deduced amino acid residues show the general characteristics of plastidial targeting sequences (von Heijne, G. et al., *Eur. J. Biochem.* 180:535–545 (1989)), consistent with the proposed subcellular location of the enzyme in plant cells. By excluding the putative transit peptide residues, the sequence corresponds to a mature protein of about 650 amino acids, with a predicted size of roughly 71 kDa. This compares to a deduced protein of 620 residues with a predicted size of 67.6 kDa described by Boronat and associates in a preliminary report on a DXPS clone from *E. coli* (Lois, L. M. et al., Third Terpnet Meeting of the European Network on Plant Isoprenoids, Poitiers, France, May 29–30 (1997)). An alignment of translated transketolase sequences (devoid of plastid-targeting peptides where appropriate) shows very high similarity/identity values between the peppermint DXPS and CLA1 from Arabidopsis (Mandel, M. A et al., *Plant J.* 9:649–658 (1996)) (85/77%), ORF 2814 (part of the puf operon in the photosynthetic gene cluster) from the purple non-sulfur photosynthetic bacterium *Rhodobacter capsulata* (Youvan, D. C. et al., *Cell* 37:949–957 (1984)) (72/56%), ORF f620 (map position 9.43 min, the presumptive DXPS of *E. coli* (Lois, L. M. et al., Third Terpnet Meeting of the European Network on Plant Isoprenoids, Poitiers, France, May 29–30 (1997)); 69/48%), and a deduced protein from the cyanobacterium *Synechocystis* sp. strain PCC6803 (Kaneko, T. et al., *DNA Res.* 3:109–136 (1996)) (65/45%) (FIG. 4). These conserved sequences appear to form a new class of transketolases that is distinct from the well-characterized transketolases involved in the pentose phosphate pathway (FIG. 4), and the extensive sequence similarity among these genes of diverse origin suggests that they all encode DXPS or a very closely related synthase. In addition, the general transketolase consensus TPP-binding motif $(GDG(X)_{7-8}E(X)_{3-4}A(X)_{11-13}NN)$ (SEQ ID NO:10) determined by Hawkins et al. (Hawkins, C. F. et al., *FEBS Let.* 255:77–82 (1989)) was observed in this new transketolase type as:

$DG(A/S)(X)T(A/G)G(Q/M)AXEAXN(N/H)AG(X)_{7-8}(I/V)(V/I)LNDN$ (SEQ ID NO:11)(residues 219–250 of the peppermint sequence).

EXAMPLE 2 cDNA Expression in *E. coli* and Product Identification

The cDNA inserts of clones pDS16 (SEQ ID NO:3), pDS29 (SEQ ID NO:5), and pDS39 (SEQ ID NO:7) were evaluated by heterologous expression for an enzyme capable of catalyzing the condensation reaction of pyruvate and GAP to a deoxypentulose phosphate (FIG. 1).

*E. coli* SOLR cells harboring pDS16, pDS29 or pDS39 were grown at 37° C. in 5 ml of LB medium supplemented with appropriate antibiotics to an $OD_{600}$ of 0.7, transferred to a new flask containing 50 ml of the same medium, and incubated at 20° C. for 2 h. After induction with 200 μmol isopropyl-1-thio-β-D-galactopyranoside (IPTG), the cells were maintained for another 14 h at 20° C. Bacteria were harvested by centrifugation (1800×g, 10 min), washed with 5 ml of assay buffer (100 mM sodium phosphate (pH 6.5) containing 3 mM $MgCl_2$, 0.1 mM EDTA, 5 mM NaF, 20 μM phenylmethanesulfonyl fluoride, and 100 μM thiamin diphosphate), and then resuspended in 1 ml of assay buffer. Cells were disrupted by brief sonication at 0–4° C., and the resulting homogenate was centrifuged as above to pellet debris. An aliquot (50 μl) of the supernatant was transferred to a 600 μl Eppendorf tube, to which 30 μM [2-¹⁴C] pyruvate (18.5 kBq) and 0.4 μM D,L-glyceraldehyde-3-phosphate (GAP) (or 0.4 μM D-GAP) were added, and the mixture was incubated at 23° C. for 30 min. The reaction was terminated by addition of 70 μl acetone and freezing at −20° C. for 20 min. Following centrifugation (14,000 rpm, bench-top centrifuge) to remove denatured protein, the supernatant was transferred to a new vial and evaporated to dryness. The residue was dissolved in 40 μl $H_2O$ and analyzed by reversed-phase $(C_{18})$ ion-pair radio-HPLC using a procedure previously described with minor modifications (McCaskill, D. & Croteau, R., *Anal. Biochem.* 215:142–149 (1993)).

Enzyme assays performed with extracts of IPTG-induced cells harboring plasmid pDS29, including the cDNA sequence set forth in SEQ ID NO:5, or pDS39, including the cDNA sequence set forth in SEQ ID NO:7, showed the GAP-dependent appearance of a labeled product with $R_t$ of 35.5 min that was formed in significantly higher amounts than in control assays (extracts from cells containing vector without insert). The radio-labeled product was isolated by semi-preparative HPLC and hydrolyzed with excess acid phosphatase, and the resulting sugar was lyophilized and silylated (100 μl bis(trimethylsilyl)trifluoroacetamide, 10 μl pyridine and 100 μg $Na_2SO_4$; 80° C. for 1 h). GC-MS analysis (of the silylated biosynthetic product and of silylated authentic 1-deoxy-D-xylulose) was performed using a Hewlett-Packard 5840A/5985B system equipped with a 30 m×0.25 mm diameter fused silica column coated with a 0.25 μm film of HP 5MS (Hewlett-Packard). The oven was programmed from 90° C. (2 min hold) at 20° C./min to 250° C. (2 min hold), then at 20° C./min to 300° C. at 10 psi He, and EI spectra were recorded at 70 eV with an electron multiplier voltage of 2200 V. Full spectra were acquired and selected diagnostic ions were monitored: m/z 307 [$M^+$–43 ($CH_3CO$)]; m/z 277 [($M^+$–73 (($CH_3)_3Si$)]; m/z 218 [$M^+$–43 ($CH_3CO$) –89 (($CH_3)_3SiO$)]; m/z 205 [$M^+$–145 ($CH_3COCHOSi(CH_3)_3$)]; m/z 204 [(($CH_3)_3SiOCHCH_2OSi(CH_3)_3)^+$]; m/z 147 [(($CH_3)_2SiOSi(CH_3)_3)^+$]; m/z 132 [(Si($CH_3)_3$)$OCH_2CHO)^+$]; m/z 117 [(($CH_3)_3SiOCH_2CH_2)^+$]; m/z 103 [(($CH_3)_3SiOCH_2)^+$]; m/z 89 [(($CH_3)_3SiO)^+$]; m/z 73 [(($CH_3)_3Si)^+$]. The silylated derivative of the biosynthetic product eluted at an $R_t$ of 6.71 min; the silylated derivative of authentic 1-deoxy-D-xylulose eluted at an $R_t$ of 6.70 min.

In accordance with the detailed procedures set forth in the preceding paragraphs, E. coli cultures transfected with phagemids derived from pDS16, including the cDNA sequence set forth in SEQ ID NO:3, pDS29, including the cDNA sequence set forth in SEQ ID NO:5, and pDS39, including the cDNA sequence set forth in SEQ ID NO:7, were each induced with isopropyl-1 thio-β-D-galactopyranoside (IPTG), the corresponding bacterial cells were harvested and homogenized, and the extracts were assayed using [2-$^{14}$C] pyruvate and D,L-glyceraldehyde-3 phosphate as co-substrates. Preparations from E. coli cells transfected with pDS29, including the cDNA sequence set forth in SEQ ID NO:5, and pDS39, including the cDNA sequence set forth in SEQ ID NO:7, yielded a prominent new radioactive component in the reaction mixture that upon reversed-phase ion-pair radio-HPLC exhibited a $R_t$ (35.5 min) consistent with that of a sugar (pentulose) phosphate (McCaskill, D. & Croteau, R., Anal. Biochem. 215:142–149 (1993)). The same enzymatic product was generated with D-glyceraldehyde-3-phosphate as co-substrate, indicating that the D-antipode is the likely natural substrate of the functionally expressed transketolase. The presumptive pentulose phosphate product from preparative enzyme incubations (E. coli transformed with pDS29, including the cDNA sequence set forth in SEQ ID NO:5) was purified by HPLC and hydrolyzed with acid phosphatase, and the resulting sugar was silylated. This derivatized product of the recombinant enzyme was then analyzed by combined capillary GC-MS and shown to possess the identical retention time (6.71±0.03 min) and mass spectrum as that of an authentic sample of silylated 1-deoxy-D-xylulose (FIGS. 2A and 2B). The combined evidence thus indicated that a cDNA encoding 1-deoxyxylulose-5-phosphate synthase (DXPS) had been acquired. DXPS activity was significantly higher in the IPTG-induced E. coli cells expressing pDS29, including the cDNA sequence set forth in SEQ ID NO:5, when compared to identically treated cells containing the same plasmid devoid of cDNA insert (SEQ ID NO:5) (7-fold higher than endogenous activity, n=7, p<0.01).

EXAMPLE 3

RNA Blot Analysis and Determination of Monoterpene Biosynthetic Rate

Peppermint oil gland secretory cell RNA was isolated from leaves of different ages, separated on a 1.5% formaldehyde-agarose gel (5 μg each lane), and blotted onto Nylon membranes. DXPS mRNA was detected with a $^{32}$P-labeled probe (SEQ ID NO:12) prepared from cDNA clone pDS29 cDNA insert (SEQ ID NO:5). Administration of $^{14}CO_2$ to peppermint plants and the isolation and quantification of the leaf monoterpenes produced were performed as described previously (Gershenzon, J. et al., Oecologia 96:583–592 (1993)).

RNA blot analyses showed a direct correlation between steady-state levels of the DXPS message and monoterpene production, as determined by (Gershenzon, J. et al., Anal. Biochem. 200:130–138 (1992)) $CO_2$ incorporation, thus suggesting activation of the non-mevalonate pathway to supply the IPP precursor for subsequent monoterpene biosynthesis in peppermint oil glands (FIG. 3).

The cloning, characterization and expression of DXPS from peppermint provides direct evidence for the operation of the mevalonate-independent pathway in plants, where, in parallel with the classical cytosolic mevalonate pathway for sterol biosynthesis (Lichtenthaler, H. K. et al., FEBS Lett. 400:271–274 (1997)), this plastidial pyruvate/GAP pathway functions to synthesize a very broad range of isoprenoids (Lichtenthaler, H. K. et al., FEBS Lett. 400:271–274 (1997)); (Zeidler J. G. et al., Z. Naturforsch 52c:15–23 (1997)); (Eisenreich, W. et al., Tetrahedron Lett. 38:3889–3892 (1997)); (Eisenreich, W. et al., Proc. Natl. Acad. Sci. USA 93:6431–6436 (1996)); and (Schwarz, M. K., PhD thesis, ETH, Zurich, Switzerland (1994)).

The novel transketolases of the present invention are highly conserved between bacteria and plants, but absent in animals which rely entirely on the classical mevalonate pathway for isoprenoid biosynthesis. The novel transketolases of the present invention are targeted to the plastids of plant cells, in which the new pathway operates, suggesting that plants have maintained the "bacterial" isoprenoid biosynthetic pathway from the prokaryotic endosymbiont that gave rise to this eukaryotic organelle.

The new pathway, termed the pyruvate/glyceraldehyde-3-phosphate pathway for which the initial steps have only recently been proposed, has been overlooked in the past in spite of the fact that, in plants and certain bacteria, it is quantitatively and functionally of greater significance than the classical mevalonate pathway. Thus, all plastid-derived isoprenoids of plants are formed by this route which yields a wide variety of structures with numerous functions in growth, development and defense.

EXAMPLE 4

Hybridization Conditions

RNA samples from the following plant species were separated on a 1.5% agarose gel containing 6% formaldehyde: Pinus taeda (1 μg messenger RNA isolated from wounded stem); Pinus taeda (20 μg total RNA isolated from wounded stem); Pseudotsuga menziesii (2 μg total RNA isolated from wounded stem); Abies grandis (20 μg total RNA isolated from wounded stem); Taxus canadensis (20 μg total RNA isolated from needles); Taxus cuspidata (20 μg total RNA isolated from needles); Oryza saliva (20 μg total RNA isolated from 20 day old developing seeds); Triticum aestivum (20 μg total RNA isolated from leaves); Lycopersicon esculentium (20 μg total RNA isolated from leaves); Hyoscyamus niger (20 μg total RNA isolated from leaves); Citrus limon (20 μg total RNA isolated from leaves); Mentha spicata (10 μg total RNA isolated from glandular trichomes); Salvia officinales (20 μg total RNA isolated from leaves); Coleus blumei (20 μg total RNA isolated from leaves).

The gel containing the separated RNA samples was blotted onto Hybond N$^+$ Nylon membrane (Amersham) and was prehybridized for one hour at 42° C. The nucleic acid sequence set forth in SEQ ID NO:5 was used as a template for generating a $^{32}$P-labelled hybridization probe. Hybridization was carried out at 42° C. for ten hours. The composition of the hybridization and prehybridization buffer was: 30% formamide, 5× Denhardt's reagent, 0.1% sodium dodecyl sulfate, 5×SSPE. The composition of 1 liter of a 50× stock solution of Denhardt's reagent is: 5 g ficoll, 5 g polyvinyl pyrolidone and 5 g bovine serum albumin. The composition of 1 liter of a 10× stock solution of SSPE is 87.7 g sodium chloride, 13.8 g $NaH_2PO_4H_2O$, 3.7 g EDTA at pH7.4. The blot was washed in 6×SSC for ten minutes at 42° C. Autoradiography revealed that the hybridization probe recognized the corresponding mRNA species encoding a 1-deoxyxylulose-5-phosphate synthase from each sample of plant mRNA.

High stringency wash conditions under which the foregoing probe derived from the nucleic acid sequence set forth in SEQ ID NO:5 will remain hybridized to Northern blotted mRNA species encoding 1-deoxyxylulose-5-phosphate synthase proteins of the present invention, or to Southern blotted DNA species encoding 1-deoxyxylulose-5-phosphate synthase proteins of the present invention are: two, fifteen minute washes in 2×SSC at room temperature (18° C. to 25° C.), followed by two, twenty minute washes in 0.2×SSC at 65° C.).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated polynucleotide fragment selected from the group consisting of:
   (a) an isolated polynucleotide fragment encoding a 1-deoxyxylulose-5-phosphate synthase obtained from *Mentha piperita*;
   (b) an isolated polynucleotide fragment encoding the 1-deoxyxylulose-5-phosphate synthase set forth in SEQ ID NO:4, 6 or 8;
   (c) an isolated polynucleotide fragment encoding a polypeptide, wherein said encoded polypeptide has 1-deoxyxylulose-5-phosphate synthase activity, and wherein said polynucleotide hybridizes to the complementary strand of the polynucleotide set forth in SEQ ID NO:3, 5, or 7 under the following set of stringent hybridization conditions:
   ten hours hybridization in 42° C. buffer consisting of 5× Denhardt's solution, 0.1% sodium dodecyl sulfate, and 5× SSPE;
   and said polynucleotide remains hybridized to the polynucleotide set forth in SEQ ID NO:3, 5 or 7 under the following set of stringent wash conditions:
   two 15 minute washes in 2× SSC at room temperature followed by two 20 minute welshes in 0.2× SSC at 65° C.

2. An isolated polynucleotide fragment of claim 1 encoding a 1-deoxyxylulose-5-phosphate synthase obtained from *Mentha piperita*.

3. An isolated polynucleotide fragment of claim 1 encoding the 1-deoxyxylulose-5-phosphate synthase set forth in SEQ ID NO:4, 6 or 8.

4. An isolated polynucleotide fragment of claim 3 encoding the 1-deoxyxylulose-5-phosphate synthase set forth in SEQ ID NO:4.

5. An isolated polynucleotide fragment of claim 3 encoding the 1-deoxyxylulose-5-phosphate synthase set forth in SEQ ID NO:6.

6. An isolated polynucleotide fragment of claim 3 encoding the 1-deoxyxylulose-5-phosphate synthase set forth in SEQ ID NO:8.

7. An isolated polynucleotide fragment of claim 1 encoding a polypeptide, wherein said encoded polypeptide has 1-deoxyxylulose-5-phosphate synthase activity, and wherein said polynucleotide hybridizes to the complementary strand of the polynucleotide set forth in SEQ ID NO:3, 5, or 7 under the following set of stringent hybridization conditions:
   ten hours hybridization in 42° C. buffer consisting of 5× Denhardt's solution, 0.1% sodium dodecyl sulfate, and 5× SSPE;
   and said polynucleotide remains hybridized to the polynucleotide set forth in SEQ ID NO:3, 5 or 7 under the following set of stringent wash conditions:
   two 15 minute washes in 2× SSC at room temperature followed by two 20 minute washes in 0.2× SSC at 65° C.

8. A replicable expression vector comprising a nucleic acid sequence selected from the group consisting of:
   (a) a nucleic acid sequence encoding a 1-deoxyxylulose-5-phosphate synthase obtained from *Mentha piperita*;
   (b) a nucleic acid sequence encoding the 1-deoxyxylulose-5-phosphate synthase set forth in SEQ ID NO:4,6 or 8;
   (c) a nucleic acid sequence encoding a polypeptide, wherein said encoded polypeptide has 1-deoxyxylulose-5-phosphate synthase activity, and wherein said nucleic acid sequence hybridizes to the complementary strand of the polynucleotide set forth in SEQ ID NO:3, 5, or 7 under the following set of stringent hybridization conditions:
   ten hours hybridization in 42° C. buffer consisting of 5× Denhardt's solution, 0.1% sodium dodecyl sulfate, and 5× SSPE;
   and said nucleic acid sequence remains hybridized to the polynucleotide set forth in SEQ ID NO:3, 5 or 7 under the following set of stringent wash conditions:

two 15 minute washes in 2× SSC at room temperature followed by two 20 minute washes in 0.2× SSC at 65° C.

9. A replicable expression vector of claim 8 comprising a nucleic acid sequence encoding a 1-deoxyxylulose-5-phosphate synthase obtained from *Mentha piperita*.

10. A replicable expression vector of claim 8 comprising a nucleic acid sequence encoding the 1-deoxyxylulose-5-phosphate synthase set forth in SEQ ID NO:4, 6 or 8.

11. A replicable expression vector of claim 10 comprising a nucleic acid sequence encoding the 1-deoxyxylulose-5-phosphate synthase set forth in SEQ ID NO:4.

12. A replicable expression vector of claim 10 comprising a nucleic acid sequence encoding the 1-deoxyxylulose-5-phosphate synthase set forth in SEQ ID NO:6.

13. A replicable expression vector of claim 10 comprising a nucleic acid sequence encoding the 1-deoxyxylulose-5-phosphate synthase set forth in SEQ ID NO:8.

14. A replicable expression vector of claim 10 comprising a nucleic acid sequence encoding a polypeptide, wherein said encoded polypeptide has 1-deoxyxylulose-5-phosphate synthase activity, and wherein said nucleic acid sequence hybridizes to the complementary strand of the polynucleotide set forth in SEQ ID NO:3, 5, or 7 under the following set of stringent hybridization conditions:

ten hours hybridization in 42° C. buffer consisting of 5× Denhardt's solution, 0.1% sodium dodecyl sulfate, and 5× SSPE;

and said nucleic acid sequence remains hybridized to the polynucleotide set forth in SEQ ID NO:3, 5 or 7 under the following set of stringent wash conditions:

two 15 minute washes in 2× SSC at room temperature followed by two 20 minute washes in 0.2× SSC at 65° C.

15. A host cell comprising a vector of claim 8.

16. A host cell comprising a vector of claim 9.
17. A host cell comprising a vector of claim 10.
18. A host cell comprising a vector of claim 11.
19. A host cell comprising a vector of claim 12.
20. A host cell comprising a vector of claim 13.
21. A host cell comprising a vector of claim 14.

22. A method of altering 1-deoxyxylulose-5-phosphate synthase activity in a host cell comprising introducing into said host cell an expression vector comprising a nucleic acid sequence selected from the group consisting of:

(a) a nucleic acid sequence encoding a 1-deoxyxylulose-5-phosphate synthase obtained from *Mentha piperita*;

(b) a nucleic acid sequence encoding the 1-deoxyxylulose-5-phosphate synthase set forth in SEQ ID NO:4, 6 or 8;

(c) a nucleic acid sequence encoding a polypeptide, wherein said encoded polypeptide has 1-deoxyxylulose-5-phosphate synthase activity, and wherein said nucleic acid sequence hybridizes to the complementary strand of the polynucleotide set forth in SEQ ID NO:3, 5, or 7 under the following set of stringent hybridization conditions:

ten hours hybridization in 42° C. buffer consisting of 5× Denhardt's solution, 0.1% sodium dodecyl sulfate, and 5× SSPE;

and said nucleic acid sequence remains hybridized to the polynucleotide set forth in SEQ ID NO:3, 5 or 7 under the following set of stringent wash conditions:

two 15 minute washes in 2× SSC at room temperature followed by two 20 minute washes in 0.2×SSC at 65° C.

23. The method of claim 22, wherein the host cell is a plant cell.

* * * * *

UNITED STATES PATENT AND TRADEMARK OFFICE
CERTIFICATE OF CORRECTION

PATENT NO.   : 6,190,895 B1
DATED        : February 20, 2001
INVENTOR(S)  : R.B.Croteau et al.

It is certified that error appears in the above-identified patent and that said Letters Patent is hereby corrected as shown below:

Item [74],
Attorney, Agent or Firm, after "O'Connor" delete ";"

Column 1,
Before line 8, before the paragraph beginning "This invention was funded,..." insert a centered heading as follows:
-- U.S. GOVERNMENT RIGHTS --
Line 35, "F. A," should read -- F. A., --
Line 40, "pp" should read -- pp. --
Lines 51-52, after "*Naturforsch*" insert -- . --
Lines 55, and 64, "PhD" should read --Ph.D. --

Column 2,
Lines 50-51, "transketolse" should read -- transketolase --
Lines 58-59, "tran-sketolases" should break as follows:
-- trans-ketolases --
Line 59, "ad" should read -- and --
Line 67, ""IPP)" should read -- (IPP) --

Column 3,
Line 4, "glyceraldehyde- 3-phosphate" should read -- glyceraldehyde-3-phosphate --
Line 14, "($R_f$=6.70" should read -- ($R_f$=6.70 --
Line 32, "P6242)," should read -- P26242), --

Column 4,
Lines 50-51, "dimethy-lallyl" should break as follows:
-- dimethyl-allyl --
Line 53, "diphosphate;;" should read -- diphosphate; --
Line 53, "3-(N-morpholion)" should read -- 3-(N-morpholino) --
Line 65, "1-deoxyxylulose5-phosphate" should read -- 1-deoxyxylulose-5-phosphate --

Column 6,
Line 27, "inset" should read -- insert --

Column 7,
Line 64, "D-glyceraldehyde-3 –phosphate" should read -- D-glyceraldehyde-3-phosphate --
Line 61, "fill-length" should read -- full-length --

UNITED STATES PATENT AND TRADEMARK OFFICE
CERTIFICATE OF CORRECTION

PATENT NO. : 6,190,895 B1
DATED : February 20, 2001
INVENTOR(S) : R.B. Croteau et al.

It is certified that error appears in the above-identified patent and that said Letters Patent is hereby corrected as shown below:

Column 8,
Line 39, "(1990)." should read -- (1990).) --
Line 41, "utilize" should read -- utilized --

Column 9,
Line 28, "BL21(D)E3)pLysS," should read -- BL21(DE3)pLysS, --

Column 10,
Line 20, "eds," should read -- eds., --

Column 12,
Line 29, "1-deoxyxylulose5-phosphate" should read -- 1-deoxyxylulose-5-phosphate --
Line 59-60, "glucose-phosphate" should read -- glucose-6-phoshate --

Column 13,
Line 41, after "regenerated" delete "an"

Column 14,
Lines 16-17, "240(4849):204-107" sholud break as follows:
-- 240(4849):204-107 --
Line 18, "et al," should read -- et al., --
Line 25, "et al," should read -- et al., --
Line 27, "rye" should read -- rye --
Lines 35-36, "*Ann Rev Plant Phys Plant Mol Biol,*" should read -- *Ann. Rev. Plant Phys. Plant Mol. Biol.,* --

Column 15,
Line 8, "insure" should read -- ensure --
Line 17, "*Sci*" should read -- *Sci.* --
Line 22, after "(HELA" insert -- , --
Line 26, "ARC," should read -- (HTC, --
Line 27, "*Bol.,*" should read -- *Biol.,* --
Line 28, "*Acad*" should read -- *Acad.* --
Line 44, "Hindi" should read -- HindIII --

Column 16,
Line 51, "$(His)_6$.Tag" should read -- $(His)_6$·Tag --

UNITED STATES PATENT AND TRADEMARK OFFICE
CERTIFICATE OF CORRECTION

PATENT NO. : 6,190,895 B1
DATED : February 20, 2001
INVENTOR(S) : R.B.Croteau et al.

It is certified that error appears in the above-identified patent and that said Letters Patent is hereby corrected as shown below:

Column 17,
Line 16, "pUCl18, pUC119," should read -- pUC118, pUC119, --
Line 53, "*Nuc.*" should read -- *Nucl.* --

Column 18,
Lines 14-15, "mutation (s)" should not break
Line 48, after "DNA" insert -- . --
Line 66, "5day-old" should read -- 5-day-old --

Column 19,
Line 1-2, "oligo
(dT)-cellulose" should not break
Line 4, "manufacturers" should read -- manufacturer's --
Line 60, "(1997)); 69/48%)" should read -- (1997)) (69/48%), --

Column 22,
Line 14, "*Naturforsch*" should read -- *Naturforsch.* --
Line 18, "PhD" should read -- Ph.D. --
Line 50, "*saliva*" should read -- *sativa* --
Line 53, "*esulentium*" should read -- *esculentum* --

Column 23,
Line 6, "pH7.4" should read -- pH 7.4 --

Column 24,
Line 8, after "65 C" delete ")"

Column 55,
Line 54, "welshes" should read -- washes --

UNITED STATES PATENT AND TRADEMARK OFFICE
CERTIFICATE OF CORRECTION

PATENT NO. : 6,190,895 B1
DATED : February 20, 2001
INVENTOR(S) : R.B. Croteau et al.

It is certified that error appears in the above-identified patent and that said Letters Patent is hereby corrected as shown below:

Column 56,
Line 54, "NO:4,6" should read -- NO:4, 6 --

Signed and Sealed this

Twenty-fifth Day of December, 2001

Attest:

JAMES E. ROGAN
*Attesting Officer*     *Director of the United States Patent and Trademark Office*